(12) United States Patent
Wang et al.

(10) Patent No.: US 11,053,238 B2
(45) Date of Patent: Jul. 6, 2021

(54) BENZIMIDAZOLE DERIVATIVES, PREPARATION METHODS AND USES THEREOF

(71) Applicant: BETTA PHARMACEUTICALS CO., LTD, Zhejiang (CN)

(72) Inventors: Yiqian Wang, Beijing (CN); Jiabing Wang, Beijing (CN); Lieming Ding, Hangzhou (CN)

(73) Assignee: BETTA PHARMACEUTICALS CO., LTD., Zhejiang (CN)

( * ) Notice: Subject to any disclaimer, the term of this patent is extended or adjusted under 35 U.S.C. 154(b) by 71 days.

(21) Appl. No.: 16/471,415

(22) PCT Filed: Dec. 22, 2017

(86) PCT No.: PCT/CN2017/117950
§ 371 (c)(1),
(2) Date: Jun. 19, 2019

(87) PCT Pub. No.: WO2018/113771
PCT Pub. Date: Jun. 28, 2018

(65) Prior Publication Data
US 2021/0130345 A1 May 6, 2021

(30) Foreign Application Priority Data

Dec. 22, 2016 (WO) ................ PCT/CN2016/111457
Apr. 14, 2017 (WO) ................ PCT/CN2017/080661

(51) Int. Cl.
*C07D 471/04* (2006.01)
*C07D 487/04* (2006.01)
*C07D 498/04* (2006.01)
*A61P 35/04* (2006.01)

(52) U.S. Cl.
CPC ............ *C07D 471/04* (2013.01); *A61P 35/04* (2018.01); *C07D 487/04* (2013.01); *C07D 498/04* (2013.01)

(58) Field of Classification Search
CPC .. C07D 471/04; C07D 487/04; C07D 498/04; A61P 35/04
USPC ..................................................... 514/230.2
See application file for complete search history.

(56) References Cited

FOREIGN PATENT DOCUMENTS

| CN | 105153119 A | 12/2015 |
| EA | 0323263 B1 | 5/2016 |
| WO | 2010/075074 A1 | 7/2010 |
| WO | 2013/067274 A1 | 5/2013 |
| WO | 2016/014904 A1 | 1/2016 |
| WO | 2016/173505 A1 | 11/2016 |
| WO | 2016173505 | * 11/2016 |
| WO | 2017/071516 A1 | 5/2017 |

OTHER PUBLICATIONS

International Search Report and Written Opinion for Application No. PCT/CN2017/117950, dated Mar. 23, 2018, 11 pages.
Patani et al., Bioisosterism: A Rational Approach in Drug Design. Chem Rev. Dec. 19, 1996;96(8):3147-3176.
PubChem CID 46220502, Abemaciclib. Retrieved online at: https://pubchem.ncbi.nlm.nih.gov/compound/46220502, 44 pages, Jul. 6, 2010.

* cited by examiner

*Primary Examiner* — Niloofar Rahmani
(74) *Attorney, Agent, or Firm* — McCarter & English, LLP; Steven G. Davis; Wei Song

(57) ABSTRACT

The present invention relates to benzimidazole compounds useful in treating for protein kinase-associated disorders. There is also a need for compounds useful in the treatment or prevention of one or more symptoms of cancer, transplant rejections. Furthermore, there is a need for methods for modulating the activity of protein kinases, such as CDK4 and/or CDK6, using the compounds provided herein.

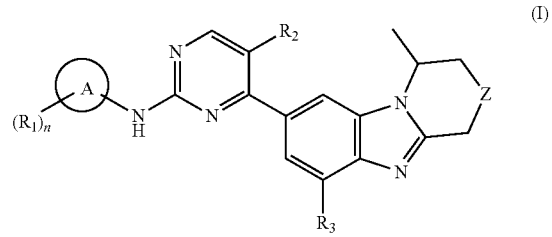

33 Claims, No Drawings

BENZIMIDAZOLE DERIVATIVES, PREPARATION METHODS AND USES THEREOF

CROSS-REFERENCE TO RELATED APPLICATIONS

This application is a U.S. national stage filing, under 35 U.S.C. § 371(c), of International Application No. PCT/CN2017/117950, filed on Dec. 22, 2017, which claims priority to International Application No. PCT/CN2017/080661, filed on Apr. 14, 2017; and International Application No. PCT/CN2016/111457, filed on Dec. 22, 2016. The entire contents of each of the aforementioned application are incorporated herein by reference.

TECHNICAL FIELD

The present invention relates to benzimidazole compounds which are useful for inhibiting cyclin-dependent kinase. More specially, the invention provides compounds and pharmaceutical compositions thereof which are used as CDK4/6 inhibitors, and methods of treatment for diseases mediated by CDK4/6, such as cancer.

BACKGROUND ART

Cyclin-dependent kinases (CDKs) mediate cell cycle progression, regulating transition from G1 to S phase and G2 to M phase. CDK activity is tightly controlled throughout the cell cycle by posttranscriptional modifications as well as the expression of cyclins and CDK inhibitors. There are four proliferative CDKs: CDK1, which predominantly regulates the transition from G2 to M phase, and CDK2/4/6, which regulate the transition from G1 to S phase.

Progression through the cell cycle is a highly regulated process. In the absence of appropriate growth signals, a family of pocket proteins including retinoblastoma protein (pRb) prevents cells from entering the DNA replication phase (S phase). The replication cycle begins when mitogens trigger signal transduction pathways, leading to increase of cellular levels of D-cyclins. D-cyclins, in turn, activate cyclin dependent kinases 4/6 (CDK4/6), which phosphorylates and inactivates pRb.

Uncontrolled cell proliferation is one of the hallmarks of cancer, and pRb inactivation is the key event that enables tumor cells to progress through the cell cycle unchecked. While some tumors delete the pRb gene itself, the majority maintains a functional pRb and instead activates CDK4/6 kinase activity. Ablation of CDK4/6 kinase activity led to complete tumor growth inhibition in many cancer types such as HR+ breast cancer, mantle cell lymphoma, glioblastoma and squamous lung cancer. Furthermore, normal fibroblast cells were shown to overcome the absence of CDK4/6 due to compensation by CDK1, whose absence is not tolerated. Taken together, this evidence suggests that a selective inhibitor of CDK4/6 may have a wider therapeutic window than pan-CDK inhibitors.

In addition to direct antineoplastic effects, CDK4/6 inhibitors are found to treat inflammatory diseases, bone diseases, metabolic diseases, neurological and neurodegenerative diseases, cardiovascular diseases, allergies and asthma, Alzheimer's diseases, and hormone related diseases. Accordingly, there has been a substantial effort in medicinal chemistry to find CDK4/6 inhibitors that are effective as therapeutic agents.

CDK1 is a key determinant of mitotic progression and it is the only CDK that can initiate the onset of mitosis. Mouse knockout experiments have shown that CDK1 is required for mammalian cell proliferation.[1] Since CDK1 is critical to the cell proliferation, toxicity caused by inhibition of CDK1 will limit the ability to achieve therapeutic level, so it is necessary to keep the selectivity of CDK1 again drug target CDK4/6.

CDK2 is structurally and functionally related to CDK1; it has a considerably broader substrate profile than CDK4 and CDK6, and phosphorylates a large number of proteins involved in cell cycle progression (for example, p27KIP1 and RB), DNA replication (for example, replication factors A and C), histone synthesis (for example, NPAT), centrosome duplication (for example, nucleophosmin (NPM)), among other processes. In contrast to CDK4 and CDK6, CDK2 is not regulated by INK4 proteins but by the CDK-interacting protein/kinase inhibitory protein (CIP/KIP) class of CDK inhibitors, which bind to CDK2-cyclin complexes and render them inactive. [1] When we design a CDK4/6 inhibitor as drug for cancer, it is better to keep the selectivity against CDK2.

In addition to the CDKs that directly promote cell cycle progression (for example, CDK4, CDK6, CDK2 and CDK1), an additional family of CDKs that regulate transcription was identified, which include CDK7, CDK8 and CDK9. CDK7 has a general role in the phosphorylation of the RNA polymerase II carboxyterminal domain that contributes to the initiation of transcription, and CDK9 also phosphorylates RNA polymerase II, thereby promoting elongation of transcription. [1] The first generation of CDK inhibitors are pan-CDK inhibitors and failed to succeed due to unmanageable toxicities. For example, flavopiridol is the most extensively investigated CDK inhibitor so far. Although flavopiridol can induce cell cycle arrest in G1 and G2 phases, in certain contexts it also induces a cytotoxic response, probably as a result of CDK7 and CDK9 inhibition that leads to suppression of transcription.[2] So, it is necessary to avoid CDK7/9 when drugs targeting CDK4/6 are designed.

So far, a variety of CDK inhibitors have been evaluated preclinically and clinically. Given the evidence described above, many research groups have embarked on the discovery of a CDK4/6 selective inhibitor, with the well-documented being Palbociclib (PD-0332991), Ribociclib (LEE-011) and Abemaciclib (LY2835219). However, there remains a need to provide more potent, selective and safer CDK4/6 inhibitors which can be used in the treatment of cell proliferative disorders such as cancer.

REFERENCE

[1]. Uzma Asghar, Agnieszka K. Witkiewicz, Nicholas C. Turner, Et al. Nat Rev Drug Discov. 2015, 14(2): 130-146.

[2]. Prithviraj Bose, Gary L Simmons, Steven Grant. Expert Opin Investig Drugs. 2013, 22(6): 723-738.

SUMMARY OF INVENTION

The present invention relates to benzimidazole compounds that are used as CDK4/6 inhibitors and for the treatment of diseases mediated by CDK4/6. The compounds of the invention have the general structures as Formula I. A compound of Formula I, or a stereoisomer, a tautomer, a polymorph, a solvate, a pharmaceutically acceptable salt, or a prodrug thereof,

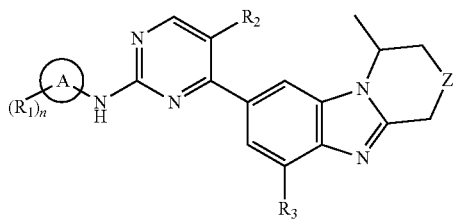

Formula I

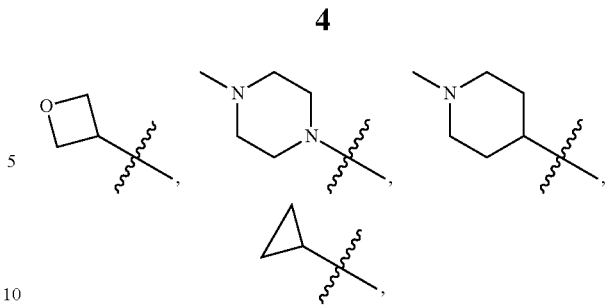

wherein, ring A is aryl or heteroaryl;

Z is selected from the group consisting of $CH_2$, NH, O and S;

$R_1$ is independently selected from the group consisting of hydrogen, halogen, CN, NO, O, $N_2$, $C_{1-8}$alkyl, $C_{1-8}$alkoxy, $C_{3-8}$cycloalkyl, aryl, heteroaryl, heterocyclyl, heterocyclyl-$(CH_2)_m$—, aryl-$C_{1-6}$alkyl-, heteroaryl-$C_{1-6}$alkyl-, —$NR_{12}R_{13}$, —$NR_{12}$—$C_{1-6}$alkylene-$NR_{12}R_{13}$, and heterocyclyl-C(O)—, wherein the $C_{1-8}$alkyl, $C_{1-8}$alkoxy, $C_{3-8}$cycloalkyl, aryl, heteroaryl, heterocyclyl, heterocyclyl-$(CH_2)_m$—, aryl-$C_{1-6}$alkyl-, heteroaryl-$C_{1-6}$alkyl-, or heterocyclyl-C(O)— are each unsubstituted or substituted with at least one substituent selected from halogen, hydroxyl, $C_{1-8}$alkyl, $C_{3-8}$cycloalkyl, heterocyclyl, —$NR_{12}R_{13}$, or —$(CH_2)_t$—OH;

$R_2$ and $R_3$ are each independently selected from H, OH, CN, $NO_2$, $NH_2$, halogen, $C_{1-8}$ alkyl, $C_{1-8}$ alkoxy, $C_{3-8}$cycloalkyl, aryl, heteroaryl, heterocyclyl; wherein the $C_{1-8}$ alkyl, $C_{1-8}$ alkoxy, $C_{3-8}$cycloalkyl, aryl, heteroaryl, heterocyclyl are each unsubstituted or substituted with at least one substituent selected from halogen, hydroxyl, $C_{1-8}$alkyl, $C_{3-8}$cycloalkyl, or heterocyclyl;

$R_{12}$ and $R_{13}$ are each independently selected from H, $C_{1-8}$alkyl, aryl, heteroaryl, heterocyclyl, or $C_{3-8}$cycloalkyl; wherein the $C_{1-8}$alkyl, aryl, heteroaryl, heterocyclyl, or $C_{3-8}$cycloalkyl are each unsubstituted or substituted with at least one substituent selected from halogen, hydroxyl, $C_{1-8}$alkyl, $C_{3-8}$cycloalkyl, or heterocyclyl;

m is 0, 1, 2, 3 or 4;

n is 0, 1, 2, 3 or 4;

t is 0, 1, 2, 3 or 4.

In some embodiments of Formula I, Z is $CH_2$.

In some embodiments of Formula I, Z is O.

In some embodiments of Formula I, ring A is a 6-membered heteroaryl comprising one or two heteroatoms of N, for example, pyridyl, pyrimidinyl, pyridazinyl and the like.

In other embodiments of Formula I, ring A is

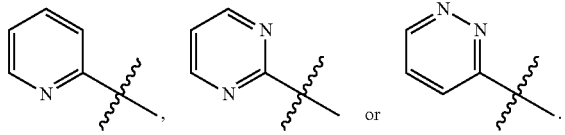 [SMILES: *c1ccccn1 ; *c1ncccn1 ; *c1cccnn1]

or

In some embodiments of Formula I, $R_1$ is heterocyclyl-$(CH_2)_m$—, or heterocyclyl-$(CH_2)_m$— substituted with $C_{1-8}$alkyl, $NR_{12}R_{13}$, 4 to 6-membered heterocyclyl, $C_{3-6}$cycloalkyl, or —$(CH_2)_t$—OH.

In other embodiments of Formula I, $R_1$ is 5 to 6-membered heterocyclyl-$CH_2$—, or 5 to 6-membered heterocyclyl-$CH_2$— substituted with $C_{1-3}$alkyl, —$N(CH_3)_2$, —$N(CH_2CH_2OH)CH_3$,

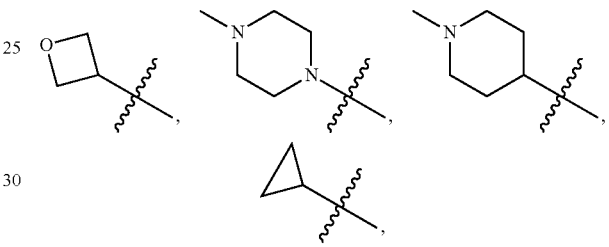

—$CH_2OH$, —$CH_2CH_2OH$, or —OH.

In other embodiments of Formula I, $R_1$ is 6-membered heterocyclyl-$CH_2$—, or 6-membered heterocyclyl-$CH_2$— substituted with methyl or ethyl.

In some embodiments of Formula I, $R_1$ is heterocyclyl, or heterocyclyl substituted with $C_{1-8}$alkyl, $NR_{12}R_{13}$, 4 to 6-heterocyclyl, $C_{3-6}$cycloalkyl, or —$(CH_2)_t$—OH.

In other embodiments of Formula I, $R_1$ is 5 to 6-membered heterocyclyl, or 5 to 6-membered heterocyclyl substituted with $C_{1-3}$alkyl, —$N(CH_3)_2$, —$N(CH_2CH_2OH)CH_3$,

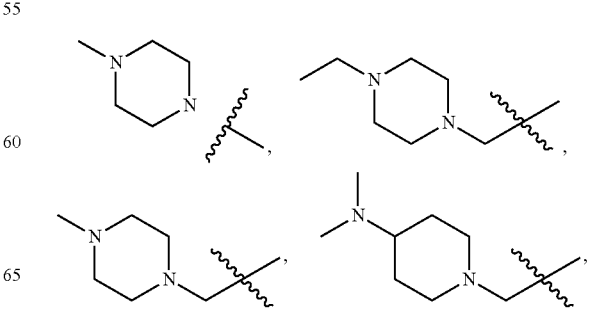

—$CH_2OH$, —$CH_2CH_2OH$, or OH.

In other embodiments of Formula I, $R_1$ is 6-membered heterocyclyl, or 6-membered heterocyclyl substituted with methyl or ethyl.

In some embodiments of Formula I, $R_1$ is 6-membered heterocyclyl-C(O)— or 6-membered heterocyclyl-C(O)— substituted with $C_{1-3}$alkyl.

In other embodiments of Formula I, $R_1$ is 6-membered heterocyclyl-C(O)— substituted with methyl.

In some embodiments of Formula I, the heterocyclyl comprises one or two heteroatoms of N or O as ring atoms.

In some embodiments of Formula I, the heterocyclyl comprises one or two heteroatoms of N as ring atoms.

In some embodiments of Formula I, $R_1$ is —$NR_{12}$—$C_{1-3}$alkylene-$NR_{12}R_{13}$.

In some embodiments of Formula I, $R_{12}$ and $R_{13}$ are each independently H, —$(CH_2)_t$—OH or $C_{1-3}$alkyl.

Preferably, $R_{12}$ and $R_{13}$ are each independently OH, $CH_2CH_2OH$, methyl or ethyl. In some embodiments of Formula I, $R_1$ is

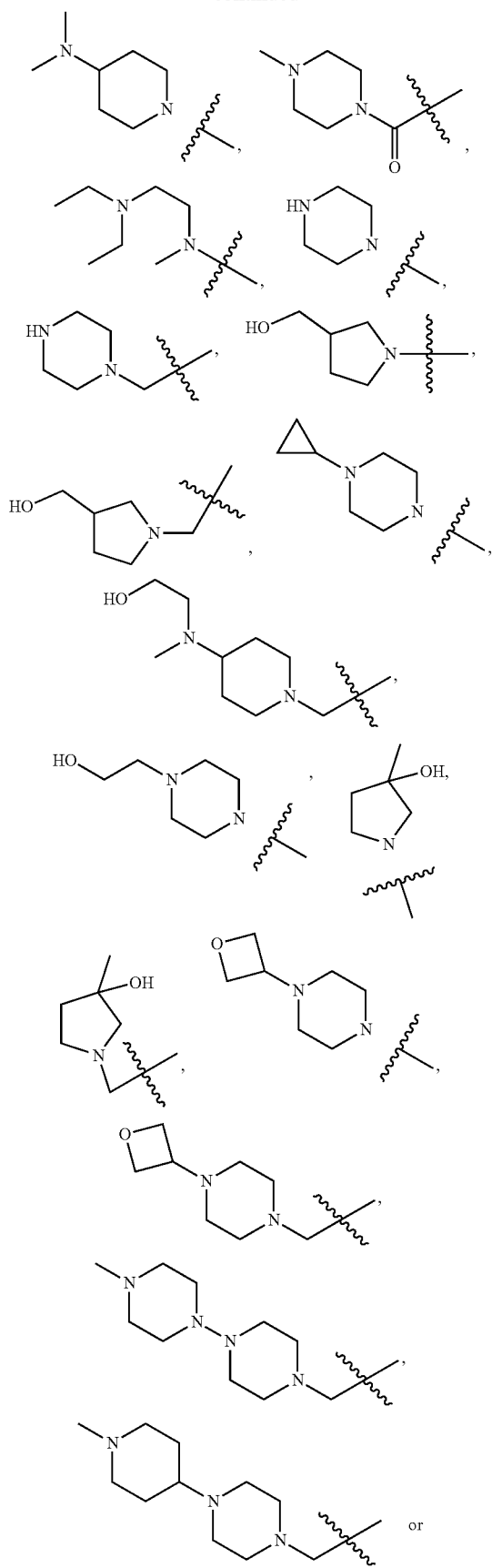

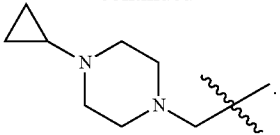

In some embodiments of Formula I, m is 1.
In some embodiments of Formula I, n is 1.
In some embodiments of Formula I, t is 0, 1, or 2.
In some embodiments of Formula I, $R_2$ and $R_3$ are each independently H, OH, halogen, $C_{1-6}$alkyl, $C_{1-6}$alkyl substituted with halogen, $C_{1-6}$alkoxy, $C_{1-6}$alkoxy substituted with halogen.

In other embodiments of Formula I, $R_2$ and $R_3$ are each independently H, OH, F, Cl, $CH_3$, $C_2CH_3$, $CF_3$, —$OCH_3$ or —$OCF_3$.

In other embodiments of Formula I, $R_2$ and $R_3$ are both F.

The present invention further provides some preferred technical solutions with regard to compound of Formula I, and the compound is:
1) 4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine;
2) N-(5-((4-ethylpiperazin-1-yl)methyl)pyridin-2-yl)-5-fluoro-4-(6-fluoro-1-methyl-1,2,3,4-tetrahydrobenzo [4,5] imidazo[1,2-a]pyridin-8-yl)pyrimidin-2-amine;
3) 5-fluoro-4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine;
4) 5-fluoro-4-(6-fluoro-1-methyl-,2,3,4-tetrahydrobenzo[4,5]imidazo[1,2-a]pyridin-8-yl)-N-(6-((4-methylpiperazin-1-yl)methyl)pyridin-3-yl)pyrimidin-2-amine;
5) 5-fluoro-4-(6-fluoro-1-methyl-,2,3,4-tetrahydrobenzo[4,5]imidazo[1,2-a]pyridin-8-yl)-N-(5-((4-methylpiperazin-1-yl)methyl)pyrimidin-2-yl)pyrimidin-2-amine;
6) N-(5-((4-(dimethylamino)piperidin-1-yl)methyl)pyrimidin-2-yl)-5-fluoro-4-(6-fluoro-1-methyl-1,2,3,4-tetrahydrobenzo[4,5]imidazo[1,2-a]pyridin-8-yl)pyrimidin-2-amine;
7) N-(5-((4-(dimethylamino)piperidin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine;
8) N-(5-(4-(dimethylamino)piperidin-1-yl)pyridin-2-yl)-5-fluoro-4-(6-fluoro-1-methyl-1,2,3,4-tetrahydrobenzo [4,5] imidazo[1,2-a]pyridin-8-yl)pyrimidin-2-amine;
9) (2-((5-fluoro-4-(6-fluoro-1-methyl-1,2,3,4-tetrahydrobenzo[4,5]imidazo[1,2-a]pyridin-8-yl)pyrimidin-2-yl)amino)pyrimidin-5-yl)(4-methylpiperazin-1-yl)methanone;
10) (6-((5-fluoro-4-(6-fluoro-1-methyl-1,2,3,4-tetrahydrobenzo[4,5]imidazo[1,2-a]pyridin-8-yl) pyrimidin-2-yl)amino)pyridin-3-yl)(4-methylpiperazin-1-yl)methanone;
11) N5-(2-(diethylamino)ethyl)-$N_2$-(5-fluoro-4-(6-fluoro-1-methyl-1,2,3,4-tetrahydrobenzo[4,5]imidazo[1,2-a]pyridin-8-yl)pyrimidin-2-yl)-N5-methylpyridine-2,5-diamine;
12) N-(5-((4-ethylpiperazin-1-yl)methyl)pyridin-2-yl)-4-(6-fluoro-1-methyl-1,2,3,4,4a,5-hexahydrobenzo [4,5]imidazo[1,2-a]pyridin-8-yl)-5-(trifluoromethyl)pyrimidin-2-amine;
13) N-(5-((4-ethylpiperazin-1-yl)methyl)pyridin-2-yl)-4-(6-fluoro-1-methyl-1,2,3,4,4a,5-hexahydrobenzo [4,5]imidazo[1,2-a]pyridin-8-yl)-5-methylpyrimidin-2-amine;
14) 5-chloro-N-(5-((4-ethylpiperazin-1-yl)methyl)pyridin-2-yl)-4-(6-fluoro-1-methyl-1,2,3,4-tetrahydrobenzo [4,5]imidazo[1,2-a]pyridin-8-yl)pyrimidin-2-amine;

15) 5-fluoro-4-(9-fluoro-4-methyl-3,4-dihydro-1H-benzo[4,5]imidazo[2,1-c][1,4]oxazin-7-yl)-N-(5-(4-methylpiperazin-1-yl)pyridin-2-yl)pyrimidin-2-amine;

16) N-(5-((4-ethylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine:

17) N-(5-(4-(dimethylamino)piperidin-1-yl)pyridin-2-yl)-5-fluoro-4-(9-fluoro-4-methyl-3,4-dihydro-1H-benzo[4,5]imidazo[2,1-c][1,4]oxazin-7-yl)pyridin-2-amine;

18) N-(5-((4-(dimethylamino)piperidin-1-yl)methyl)pyridin-2-yl)-5-fluoro-4-(9-fluoro-4-methy 1-3,4-dihydro-1H-benzo[4,5]imidazo[2,1-c][1,4]oxazin-7-yl)pyrimidin-2-amine;

19) 5-fluoro-4-(9-fluoro-4-methyl-3,4-dihydro-1H-benzo[4,5]imidazo[2,1-c][1,4]oxazin-7-yl)-N-(5-(piperazin-1-yl)pyridin-2-yl)pyrimidin-2-amine;

20) 5-fluoro-4-(9-fluoro-4-methyl-3,4-dihydro-1H-benzo[4,5]imidazo[2,1-][1,4]oxazin-7-yl)-N-(5-(piperazin-1-ylmethyl)pyridin-2-yl)pyrimidin-2-amine;

21) N-(5-fluoro-4-(9-fluoro-4-methyl-3,4-dihydro-1H-benzo[4,5]imidazo[2,1-c][1,4]oxazin-7-yl)pyrimidin-2-yl)-6-(4-methylpiperazin-1-yl)pyridazin-3-amine;

22) 6-((4-ethylpiperazin-1-yl)methyl)-N-(5-fluoro-4-(9-fluoro-4-methyl-3,4-dihydro-1H-benzo [4,5]imidazo[2,1-c][1,4]oxazin-7-yl)pyrimidin-2-yl)pyridazin-3-amine;

23) (1-(6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)pyrrolidin-3-yl)methanol;

24) (1-((6-((5-fluoro-4-(9-fluoro-4-methyl-3,4-dihydro-11H-benzo[4,5]imidazo[2,1-c][1,4]oxazin-7-yl)pyrimidin-2-yl)amino)pyridin-3-yl)methyl)pyrrolidin-3-yl)methanol;

25) N-(5-(4-cyclopropylpiperazin-1-yl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

26) N-(5-((4-cyclopropylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine:

27) 2-((1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)piperidin-4-yl)(methyl)amino)ethan-1-ol;

28) 1-(6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)-3-methylpyrrolidin-3-ol;

29) 1-((6-((5-fluoro-4-(9-fluoro-methy-3,4-dihydro-1H-benzo[2,1-c][1,4]oxazin-7-yl)pyrimidin-2-yl)amino)pyridin-3-yl)methyl)-3-methylpyrrolidin-3-ol;

30) 5-fluoro-4-(9-fluoro-4-methyl-3,4-dihydro-1H-benzo[4,5]imidazo[2,1-c][1,4]oxazin-7-yl)-N-(5-((4-(oxetan-3-yl)piperazin-1-yl)methyl)pyridin-2-yl)pyrimidin-2-amine;

31) 5-fluoro-4-(9-fluoro-4-methyl-3,4-dihydro-H-benzo[4,5]imidazo[2,1-c][1,4]oxazin-7-yl)-N-(5-(4-(oxetan-3-yl)piperazin-1-yl)pyridin-2-yl)pyrimidin-2-amine;

32) N-(5-((4-ethylpiperazin-1-yl)methyl)pyridin-2-yl)-5-fluoro-4-(9-fluoro-4-methyl-1,2,3,4-tetrahydrobenzo [4,5] imidazo[1,2-a]pyrazin-7-yl)pyrimidin-2-amine;

33) 5-fluoro-4-(9-fluoro-4-methyl-3,4-dihydro-1H-benzo[4,5]imidazo[2,1-c][1,4]oxazin-7-yl)-N-(5-((4'-methyl-[1,1'-bipiperazin]-4-yl)methyl)pyridin-2-yl)pyrimidin-2-amine;

34) 5-fluoro-4-(9-fluoro-4-methyl-3,4-dihydro-H-benzo[4,5]imidazo[2,1-c][1,4]oxazin-7-yl)-N-(5-((4-(1-methylpiperidin-4-yl)piperazin-1-yl)methyl)pyridin-2-yl)pyrimidin-2-amine.

Surprisingly, the highly purified (−) enantiomer of the compound of Formula I is advantageous over the (+) enantiomer in biological activity. For example, the optically pure (−) enantiomer of compound 2 (N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine) is more potent than its (+) enantiomer.

Unless otherwise indicated, "(−)" in the present invention means that the optical rotation is a negative value; and "(−)" means that the optical rotation is a positive value. The present compound described herein can be (−) isomer of the compound and/or (+) isomer of the compound.

The present invention also provides pharmaceutical compositions comprising a therapeutically effective amount of a compound of Formula I or a therapeutically acceptable salt thereof and a pharmaceutically acceptable excipient.

In some embodiments, the said compound in a weight ratio to the said excipient within the range from about 0.001 to about 10.

The present invention additionally provides a compound of the present invention, a pharmaceutically acceptable salt thereof or a pharmaceutical composition above mentioned for the preparation of a medicament.

In some embodiments, the medicament is used for the treatment of cancer, such as colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, brain cancer or lung cancer.

In some embodiments, the medicament is used as an inhibitor of CDK, preferably CDK4 and/or CDK6.

The present invention provides a method of treating of cancer in a subject, comprising administering to the subject in need of a therapeutically effective amount of a compound of the present invention, a pharmaceutically acceptable salt thereof or above-mentioned pharmaceutical composition. In particular, the cancer is selected from the group consisting of colon cancer, rectal cancer, mantle cell lymphoma, multiple myeloma, breast cancer, prostate cancer, glioblastoma, squamous cell esophageal cancer, liposarcoma, T-cell lymphoma, melanoma, pancreatic cancer, brain cancer or lung cancer.

This invention further provides a method of treating a disease mediated by CDK, for example CDK4 and/or CDK 6 in a subject, comprising administering to the subject in need of a therapeutically effective amount of a compound of the present invention, a pharmaceutically acceptable salt thereof or above-mentioned pharmaceutical composition.

The general chemical terms used in the formula above have their usual meanings. For example, the term "halogen", as used herein, unless otherwise indicated, means fluoro, chloro, bromo or iodo. The preferred halogen groups include F, Cl and Br.

As used herein, unless otherwise indicated, alkyl includes saturated monovalent hydrocarbon radicals having straight, or branched moieties. For example, alkyl radicals include methyl, ethyl, propyl, isopropyl, n-butyl, isobutyl, sec-butyl, t-butyl, n-pentyl, 3-(2-methyl) butyl, 2-pentyl, 2-methylbutyl, neopentyl, n-hexyl, 2-hexyl, 2-methylpentyl and the like. Similarly, $C_{1-8}$, as in $C_{1-8}$alkyl is defined to identify the group as having 1, 2, 3, 4, 5, 6, 7 or 8 carbon atoms in a linear or branched arrangement.

Alkenyl and alkynyl groups include straight, or branched chain alkenes and alkynes. Likewise. "$C_{2-8}$ alkenyl" and "$C_{2-8}$ alkynyl" means an alkenyl or alkynyl radicals having 2, 3, 4, 5, 6, 7 or 8 carbon atoms in a linear or branched arrangement.

Alkoxy are oxygen ethers formed from the previously described straight, or branched chain alkyl groups, that is —O-alkyl.

As used herein, "a", "an", "the", "at least one", and "one or more" are used interchangeably. Thus, for example, a composition comprising "a" pharmaceutically acceptable excipient can be interpreted to mean that the composition includes "one or more" pharmaceutically acceptable excipients.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclyl", as used herein, unless otherwise indicated, represents an unsubstituted or substituted stable three to eight membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and tetrahydrooxadiazolyl.

The term "heteroaryl", as used herein, unless otherwise indicated, represents an unsubstituted or substituted stable five or six membered monocyclic aromatic ring system or an unsubstituted or substituted nine or ten membered benzofused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "cycloalkyl" refers to a cyclic saturated alkyl chain having from 3 to 12 carbon atoms, for example, cyclopropyl, cyclobutyl, cyclopentyl, or cyclohexyl.

The term "substituted" refers to a group in which one or more hydrogen atoms are each independently replaced with the same or different substituent(s). Typical substituents include, but are not limited to, halogen (F, Cl, Br or I), $C_{1-8}$ alkyl, $C_{3-12}$ cycloalkyl, —$OR^1$, $SR^1$, =O, =S, —$C(O)R^1$, —$C(S)R^1$, =$NR^1$, —$C(O)OR^1$, —$C(S)OR^1$, —$NR^1R^2$, —$C(O)NR^1R^2$ cyano, nitro, —$S(O)_2R^1$, —$OS(O_2)OR^1$, —$OS(O)_2R^1$, —$OP(O)OR^1)(OR^2)$; wherein $R^1$ and $R^2$ is independently selected from —H, $C_{1-6}$ alkyl, $C_{1-6}$ haloalkyl. In some embodiments, the substituent(s) is independently selected from the group consisting of —F, —Cl, —Br, —I, —OH, trifluoromethoxy, ethoxy, propyloxy, iso-propyloxy, n-butyloxy, isobutyloxy, t-butyloxy, —$SCH_3$, —$SC_2H_5$, formaldehyde group, —$C(OCH_3)$, cyano, nitro, $CF_3$, —$OCF_3$, amino, dimethylamino, methyl thio, sulfonyl and acetyl.

Examples of substituted alkyl groups include, but not limited to, 2-aminoethyl, 2-hydroxyethyl, pentachloroethyl, trifluoromethyl, methoxymethyl, pentafluoroethyl and piperazinylmethyl.

Examples of substituted alkoxy groups include, but not limited to, aminomethoxy, trifluoromethoxy, 2-diethylaminoethoxy, 2-ethoxycarbonylethoxy, 3-hydroxypropoxy.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids, particularly preferred are formic and hydrochloric acid. Since the compounds of Formula I are intended for pharmaceutical use they are preferably provided in substantially pure form, for example at least 60% pure, more suitably at least 5% pure, especially at least 98% pure (% are on a weight for weight basis).

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. For example, any pharmaceutically acceptable salt, ester, ester salt or other derivative of a compound of this application that, upon administration to a recipient, is capable of providing, either directly or indirectly, a compound of the present application or a pharmaceutically active metabolite or residues. Particularly preferred derivatives or prodrugs are those compounds that can increase the bioavailability of a compound of the present application when administered to a patient (eg, which can make an orally administered compound more readily absorbed into the blood), or facilitate delivery of the parent compound to a biological organism or those that are delivered by a site of action (eg, the brain or lymphatic system). Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described herein can contain one or more asymmetric centers and may thus give rise to diastereomers and optical enantiomers. The present invention includes all such possible diastereomers as well as their racemic mixtures, their substantially pure resolved enantiomers, all possible geometric enantiomers, and pharmaceutically acceptable salts thereof.

It has now been discovered that the optically pure (−) enantiomer of the present compound is a more potent CDK4/6 inhibitor. The present invention includes methods for treating a disease mediated by CDK4/6 in a subject, which comprises administering to said subject an amount of (−) enantiomer or a pharmaceutically acceptable salt thereof, substantially free of its (+) enantiomer, said amount being sufficient to alleviate the disease, but insufficient to cause said adverse effects.

The term "substantially free of its (+) enantiomer" as used herein means that the composition contains a greater proportion or percentage of the (−) enantiomer in relation to the (+) enantiomer, said percentage being based on the total amount of the mixture. In a embodiment, the term "substantially free of its (+) enantiomer" means that the composition contains at least 60% by weight of (−) enantiomer, and 40% by weight or less of (−) enantiomer. In a preferred embodiment, the term "substantially free of its (+) enantiomer" means that the composition contains at least 70% by weight of (−) enantiomer, and 30% by weight or less of (+) enantiomer. In another embodiment, the term "substantially free of its (+) enantiomer" means that the composition contains at least 80% by weight of (−) enantiomer, and 20% by weight or less of (+) enantiomer. Furthermore, the term "substantially free of its (+) enantiomer" means that the composition contains at least 90% by weight of (−) enantiomer, and 10% by weight or less of (+) enantiomer. Even further, the term "substantially free of its (+) enantiomer" means that the composition contains at least 95% by weight of (−) enantiomer, and 5% by weight or less of (+) enantiomer. Moreover, the term "substantially free of its (+) enantiomer" means that the composition contains at least 99% by weight of (−) enantiomer, and 1% by weight or less of (+) enantiomer.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula I exists, the present invention includes any possible tautomers and pharmaceutically acceptable salts thereof, and mixtures thereof, except where specifically stated otherwise.

When the compound of Formula I and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "composition" is herein meant to include products that include the specified amounts of the specified ingredients, as well as any product that is produced, directly or indirectly, from the specified combination of specified ingredients. Therefore, pharmaceutical compositions containing the compounds of the present invention as active ingredients and methods of preparing the compounds of the invention are also parts of this invention. In addition, some of the crystalline forms of the compounds may exist as polymorphs, and such polymorphs are included in the present invention. In addition, some of the compounds may form solvates with water (ie, hydrates) or common organic solvents, and such solvates also fall within the scope of the present invention.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, a stereoisomer, a tautomer, a polymorph, a solvate, a pharmaceutically acceptable salt, or a prodrug of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include such as lactose, terra alba, sucrose, talc, gelatin, agar, pectin, acacia, magnesium stearate, and stearic acid. Examples of liquid carriers include such as sugar syrup, peanut oil, olive oil, and water. Examples of gaseous carriers include such as carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, glioblastoma or lung cancer, may be effectively treated by the administration of from about 0.01 to 50 mg of the compound per kilogram of body weight per day, or alternatively about 0.5 mg to about 3.5 g per patient per day.

It is understood, however, that lower or higher doses than those recited above may be required. Specific dose level and treatment regimens for any particular subject will depend upon a variety of factors, including the activity of the specific compound employed, the age, body weight, general health, sex, diet, time of administration, route of administration, rate of excretion, drug combination, the severity and course of the particular disease undergoing therapy, the subject disposition to the disease, and the judgment of the treating physician.

These and other aspects will become apparent from the following written description of the invention.

EXAMPLES

It is to be understood that the foregoing general description and the following detailed description are exemplary and explanatory only and are not restrictive of any subject matter claimed. All parts and percentages are by weight and all temperatures are degrees Celsius, unless explicitly stated otherwise. The compounds described herein can be obtained from commercial sources or synthesized by conventional methods as shown below using commercially available starting materials and reagents. The following abbreviations have been used in the examples:

ATP: Adenosine triphosphate;
Boc$_2$O: Di-tert-butyl dicarbonate;
con-H$_2$SO$_4$: concentrated sulfuric acid;
Crk: CT10 (Chicken Tumor Retrovirus 10);
DCM: dichloromethane;
DEA: Diethylamine;
DEAD: Diethyl azodicarboxylate;
DIEA: N,N-Diisopropylethylamine;
DMEM: Dulbecco's Modified Eagle Media;
DMF: N,N-Dimethylformamide;
DMA: N,N-Dimethyacetamide;
DMAP: 4-N,N-Dimethylaminopyridine;
DMSO: Dimethyl sulfoxide;
DTT: DL-Dithiothreitol;
EA: Ethyl acetate;
EDC: I-ethyl-3-(3-dimethylaminopropyl)carbodiimide;
EDTA: eathylene diamine tetraacetic acid;
EtOH: ethyl alcohol;
FBS: fetal bovine serum;
GSR: Glutathione-S-Transferase;
HAT U: O-(7-Azabenzotriazol-1-yl)-N,N,N',N'-tetramethyluronium hexafluorophosphate;
HEPES: 4-(2-hydroxyethyl) piperazine-1-erhaesulfonic acid;
Hex: n-hexane;
h or hr: Hour;
IPA: isopropanol
KOAc: potassium acetate;
KTB: potassium tert-butoxide;
MeOH: methanol;
min: Minute;
MsCl: methylsulfonyl chloride;
MTS: 3-(4,5-dimethylthiazol-2-yl)-5-(3-carboxymethoxyphenyl)-2-(4-sulfophenyl)-2H-tetrazoli um;
NaBH$_4$: sodium borohydride;
NaBH(OAc)$_3$: Sodium triacetoxyborohydride;
P(Cy)$_3$: Tricyclohexyl phosphine;
Pd$_2$(dba)$_3$: Tris(dibenzylideneacetone)dipalladium
Pd(dppf)Cl$_2$: [1,1-Bis(diphenylphosphino)ferrocene]dichloropalladium Pd(OAc)$_2$: Palladium acetate;
PE: Petroleum ether;
PMS: phenazine methosulfate;
POCl$_3$: phosphorus oxychloride;
P/S: Penicillin/Streptomycin Solution;
RT or it: room temperature;
SDS: Sodium Dodecyl Sulfate;
SDS-PAGE: Sodium Dodecyl Sulfate PolyAcrylamide Electrophoresis Gel;
TBAB: Tetrabutyl ammonium bromide;
TEA: Triethylamine;
THF: tetrahydrofuran;
TLC: Thin layer chromatography;
Tol: Toluene.

Preparation 1: 5-(4-methylpiperazin-1-yl)pyridin-2-amine (Intermediate M1)

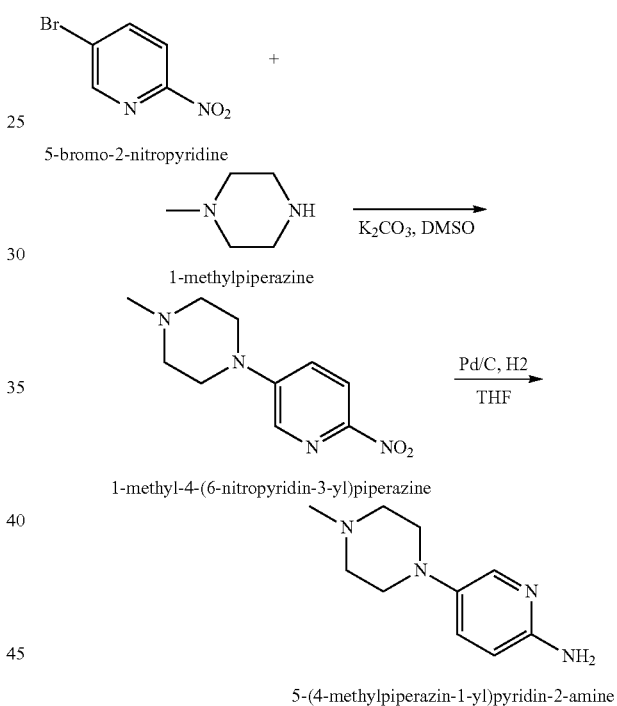

Add 1-Methylpiperazine (1.180 g) and K$_2$CO$_3$ (2.720 g) successively to a solution of 5-bromo-2-nitropyridine (2.010 g) in DMSO (20 mL). Let the reaction stir at 82° C. for 15 hrs in an oil bath. Add water (50 mL), extract with DCM (20 mL×8), the combined organic phase was dried over anhydrous Na$_2$SO$_4$, concentrated under reduced pressure, purified by column chromatography (DCM/MeOH=10/1) to give 1.940 g of 1-methyl-4-(6-nitropyridin-3-yl)piperazine.

Add Pd/C (0.194 g) to a solution of 1-methyl-4-(6-nitropyridin-3-yl)piperazine (1.940 g) in THF (25 mL) under hydrogen for 2 hrs at RT. The filtrate was collected by filtration and then concentrated to give 1.480 g of 5-(4-methylpiperazin-1-yl)pyridin-2-amine.

MS(ES$^+$): m/z=193.1 (M+H)$^+$.

Prepare the following intermediates (shown in Table 1) essentially as described for 5-(4-methylpiperazin-1-yl)pyridin-2-amine (herein referred as Intermediate M1) using the corresponding piperazine derivative.

TABLE 1

| Intermediate | Compound | Structure | Physical Data (MS) (M + H)+ |
|---|---|---|---|
| M2 | 5-(piperazin-1-yl)pyridin-2-amine | 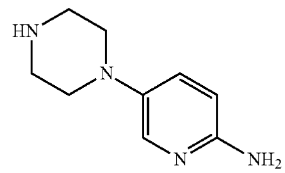 | 179.1 |
| M3 | 2-(4-(6-aminopyridin-3-yl)piperazin-1-yl)ethan-1-ol | 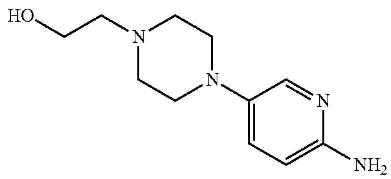 [SMILES: Nc1ccc(N2CCN(CCO)CC2)cn1] | 223.1 |

Preparation 4: 6-((4-methylpiperazin-1-yl)methyl)pyridin-3-amine (Intermediate M4)

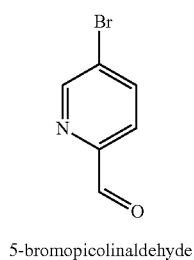

5-bromopicolinaldehyde

(5-bromopyridin-2-yl)methanol

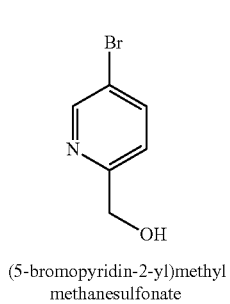

(5-bromopyridin-2-yl)methyl methanesulfonate

-continued

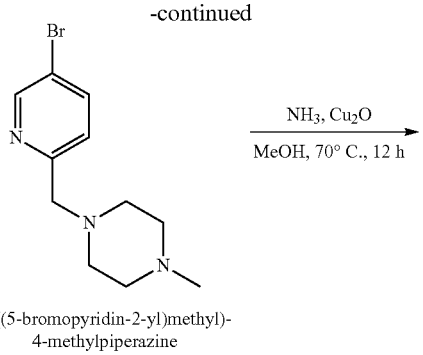

1-((5-bromopyridin-2-yl)methyl)-4-methylpiperazine

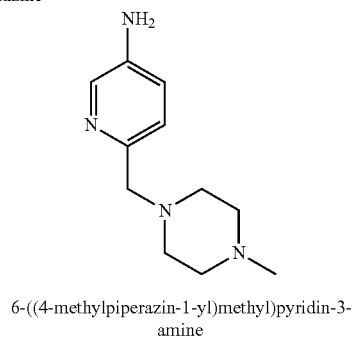

6-((4-methylpiperazin-1-yl)methyl)pyridin-3-amine

Add NaBH$_4$ (1.220 g) to a solution of 5-Bromopicolinaldehyde (2.010 g) in MeOH (30 mL) at 0° C. in an ice bath, after the addition of NaBH$_4$ is complete, remove the ice bath, warm to room temperature naturally. After stirring for 2 hrs at RT, the reaction mixture was quenched with water (50 mL) at 0° C. Extract with EA (50 mL×2), the combined organic phase washed with saturated NaCl solution and dried over anhydrous Na$_2$SO$_4$, concentrated to give 1.940 g of (5-bromopyridin-2-yl) methanol.

A solution of (5-bromopyridin-2-yl) methanol (1.940 g) in THF (20 mL) is cooled to 0° C. in an ice bath, then add methylsulfonyl chloride (1.780 g) drop wise to the solution. After the addition of methylsulfonyl chloride is complete, remove the ice bath, warm to room temperature naturally. After stirring for 2 hrs at RT, the reaction mixture was quenched with water (50 mL). Extract with EA (50 mL×2), the combined organic phase washed with saturated NaCl solution (50 mL) and dried over anhydrous Na$_2$SO$_4$, concentrated to give 2.750 g of crude product (5-bromopyridin-2-yl) methyl methanesulfonate.

Add K₂CO₃ (2.870 g) and 1-Methylpiperazine (1.560 g) successively to a solution of (5-bromopyridin-2-1) methyl methanesulfonate (2.750 g) in acetonitrile (30 mL), heat to 50° C. in an oil bath and react for 2 hrs. Then cool to room temperature, add water, extract with EA (50 mL-3), the combined organic phase washed with saturated NaCl solution (50 mL) and dried over anhydrous Na₂SO₄, concentrated and purified by column chromatography (DCM/MeOH=10/1) to give 2.010 g of 1-((5-bromopyridin-2-yl)methyl)-4-methylpiperazine.

Add MeOH (20 mL) to a 100 mL sealed tube under ammonia at −78° C., then add 1-((5-bromopyridin-2-yl)methyl)-4-methylpiperazine (1.000 g) and cuprous oxide (0.532 g) successively until the volume of solution rising to 30 mL. Remove the outside bath, warm to room temperature naturally, then heat to 70° C. and react for 12 hrs. The filtrate was collected by filtration concentrated and purified by column chromatography (DCM/MeOH=15/1) to give 0.730 g of 6-((4-methylpiperazin-1-yl)methyl)pyridin-3-amine.

MS(ES⁺): m/z=207.2 (M+H)⁺.

Prepare the following intermediates (shown in Table 2) essentially as described for 6-((4-methylpiperazin-1-yl)methyl)pyridin-3-amine (herein referred as Intermediate M4) using the corresponding piperazine derivative.

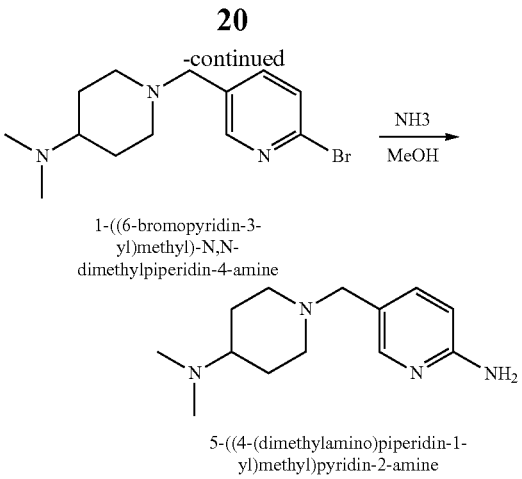

1-((6-bromopyridin-3-yl)methyl)-N,N-dimethylpiperidin-4-amine 5-((4-(dimethylamino)piperidin-1-yl)methyl)pyridin-2-amine Add NaBH₄ (1.640 g) to a solution of 2-Bromo-5-formylpyridine (2.010 g) in THF (20 mL) at 0° C. in an ice bath, after the addition of NaBH₄ is complete, remove the ice bath, warm to room temperature naturally. After stirring for 2 hrs at RT, the reaction mixture was quenched with water (50

TABLE 2

| Intermediate | Compound | Structure | Physical Data (MS) (M + H)⁺ |
|---|---|---|---|
| M5 | 5-((4-ethylpiperazine-1-yl)methyl)pyridin-2-amine | 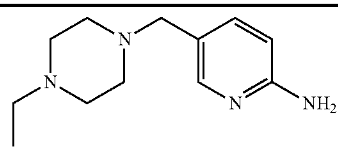 | 221.2 |
| M6 | 5-(piperazin-1-ylmethyl)pyridin-2-amine | 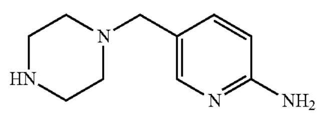 | 193.1 |

Preparation 7: 5-((4-(dimethylamino)piperidin-1-yl)methyl)pyridin-2-amine (Intermediate M7)

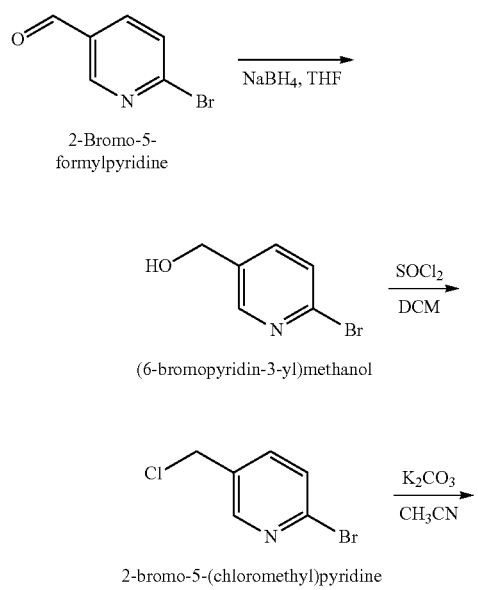

2-Bromo-5-formylpyridine (6-bromopyridin-3-yl)methanol 2-bromo-5-(chloromethyl)pyridine mL), extract with EA (50 mL×2), the combined organic phase dried over anhydrous Na₂SO₄, concentrated and purified by column chromatography (PE/EA=5/1) to give 1.900 g of (6-bromopyridin-3-yl) methanol.

A solution of (6-bromopyridin-3-yl)methanol (1.000 g) in DCM (10 mL) is cooled to 0° C. in an ice bath and added to thionyl chloride (1.260 g) dropwise, after the addition is complete, remove the ice bath, the solution is warmed to room temperature naturally with stirring for 2 hrs, then directly concentrated to give 1.050 g of 2-bromo-5-(chloromethyl)pyridine.

Add N,N-Dimethylpiperidin-4-amine (0.586 g) and K₂CO₃ (1.160 g) to a solution of 2-bromo-5-(chloromethyl)pyridine (0.853 g) in acetonitrile (10 mL). Add water (30 mL), extract with EA (50 mL×3), the combined organic phase dried over anhydrous Na₂SO₄, concentrated and purified by column chromatography (DCM/MeOH=10/J) to give 0.730 g of 1-(6-bromopyridin-3-yl)methyl)-N,N-dimethylpiperidin-4-amine.

Add MeOH (20 mL) to a 100 mL sealed tube under ammonia at −78° C., then add 1-((6-bromopyridin-3-yl)methyl)-N,N-dimethylpiperidin-4-amine (0.35 mg) and cuprous oxide (0.168 g) successively until the volume of solution rising to 30 mL. Remove the outside bath, warm to room temperature naturally, then heat to 70° C. and react for 12 hrs. The filtrate was collected by filtration, concentrated and purified by column chromatography (DCM/MeOH=10/1) to give 0.260 g of 5-((4-(dimethylamino)piperidin-1-yl)methyl)pyridin-2-amine.

MS(ES⁺): m/z=235.2 (M+H)⁺.

Prepare the following intermediates (shown in Table 3) essentially as described for 5-((4-(dimethylamino)piperidin-1-yl)methyl)pyridin-2-amine (herein referred as Intermediate M7) using the corresponding piperidine derivative.

TABLE 3

| Intermediate | Compound | Structure | Physical Data (MS) (M + H)+ |
|---|---|---|---|
| M8 | 5-(4-(dimethylamino)piperidin-1-yl)pyridin-2-amine | 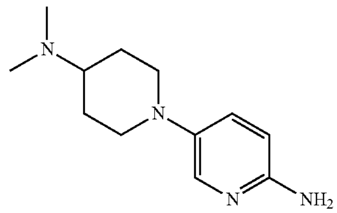 [SMILES: CN(C)C1CCN(c2ccc(N)nc2)CC1] | 221.3 |
| M9 | 2-((1-(6-aminopyridin-3-yl)piperidin-4-yl)(methyl)amino)ethan-1-ol | 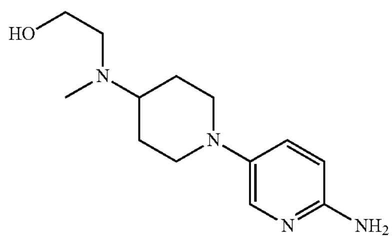 [SMILES: CN(CCO)C1CCN(c2ccc(N)nc2)CC1] | 251.2 |
| M10 | 2-((1-((6-aminopyridin-3-yl)methyl)piperidin-4-yl)(methyl)amino)ethan-1-ol | 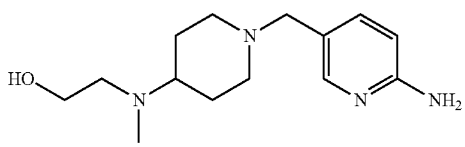 [SMILES: CN(CCO)C1CCN(Cc2ccc(N)nc2)CC1] | 265.2 |

Preparation 11: 5-((4-methylpiperazin-1-yl)methyl)pyrimidin-2-amine hydrochloride (Intermediate M11)

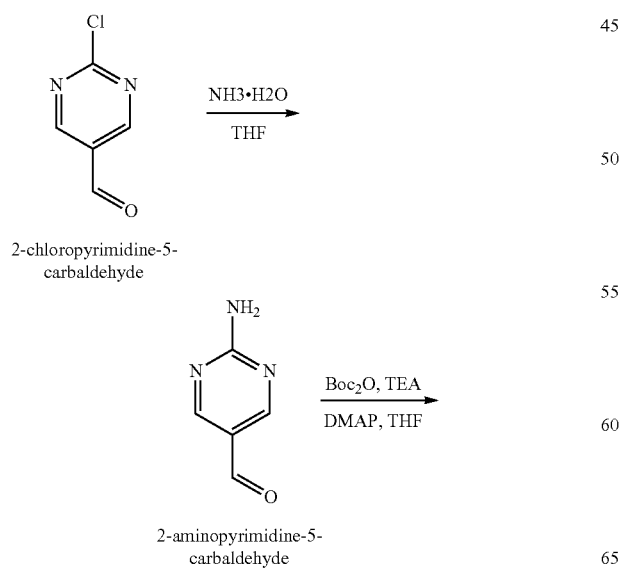

2-chloropyrimidine-5-carbaldehyde 2-aminopyrimidine-5-carbaldehyde

-continued

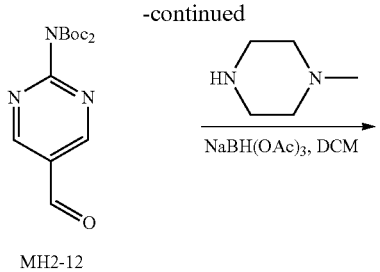

MH2-12

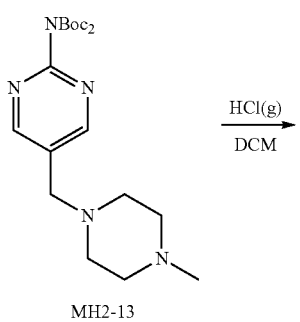

MH2-13

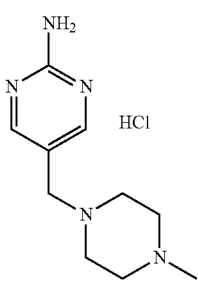

5-((4-methylpiperazin-1-yl)methyl)pyrimidin-2-amine hydrochloride

Add aqueous ammonia (25%) (1.200 g) to a solution of 2-Chloropyrimidine-5-carbaldehyde (0.500 g) in THF (50 mL), stirring for 12 hrs. Add water (80 mL), extract with DCM (80 mL×8), the combined organic phase dried over anhydrous $Na_2SO_4$, concentrated to give 0.540 g of crude product 2-aminopyrimidine-5-carbaldehyde.

Add $Boc_2O$ (2.817 g), triethylamine (1.310 g) and DMAP (0.054 g) successively to a solution of 2-aminopyrimidine-5-carbaldehyde (0.540 g) in THF (30 mL) with stirring for 2 hrs. Add water, extract with EA (50 mL×2), the combined organic phase dried over anhydrous $Na_2SO_4$, concentrated and purified by column chromatography (PE/EA=5/1) to give 0.514 g of compound MH2-12.

Add 1-Methylpiperazine) (0.109 g) and anhydrous magnesium sulfate (0.216 g) successively to a solution of compound MH2-12 (0.290 g) in DCM (1 mL) with stirring for 2 hrs, then react for 3 hrs at RT after adding Sodium triacetoxyborohydride, the reaction mixture was quenched with water (20 mL), extract with DCM (2 mL×3), the combined organic phase dried over anhydrous $Na_2SO_4$, concentrated and purified by column chromatography (DCM/MeOH=10/1) to give 0.350 g of compound MH2-13.

A solution of compound MH2-13 (0.350 g) in DCM is reacted for 2 hrs under hydrochloric acid gas at RT, the reaction mixture is concentrated to give 0.210 g of 5-((4-methylpiperazin-1-yl)methyl) pyrimidin-2-amine hydrochloride.

MS(ES$^+$): m/z=244.1 (M+H)$^+$.

Prepare the following intermediate (shown in Table 4) essentially as described for 5-((4-methylpiperazin-1-yl)methyl)pyrimidin-2-amine (herein referred as Intermediate M11) hydrochloride using the corresponding piperidine derivative instead of piperazine derivative.

TABLE 4

| Intermediate | Compound | Structure | Physical Data (MS) (M + H)$^+$ |
|---|---|---|---|
| M10 | 5-((4-dimethylamino)piperidin-1-yl)methyl)pyrimidin-2-amine | 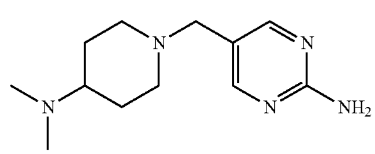 [SMILES: CN(C)C1CCN(Cc2cnc(N)nc2)CC1] | 236.2 |

Preparation 13: (2-aminopyrimidin-5-yl)(4-methylpiperazin-1-yl)methanone (Intermediate M13)

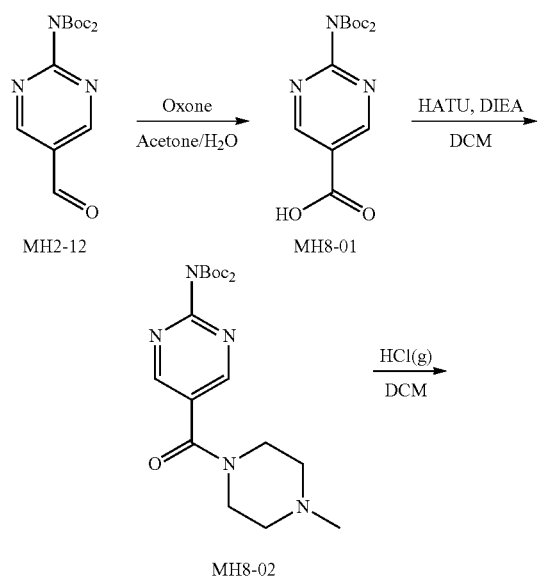

(20 mL), extract with DCM (20 mL×3), the combined organic phase dried over anhydrous $Na_2SO_4$, concentrated and purified by column chromatography (DCM/MeOH=50/1) to give 0.250 g of compound MH8-02.

A solution of compound MH8-02 (0.150 g) in DCM (10 mL) is reacted for 2 hrs under hydrochloric acid gas at RT, add water (10 mL), then adjust pH to 8-9 with $Na_2CO_3$, the resulting aqueous solution was extracted with mixed solvent (DCM/MeOH=10/1) (20 mL×5). The combined organic phase was dried over anhydrous $Na_2SO_4$, concentrated to give 0.060 g of (2-aminopyrimidin-5-yl)(4-methylpiperazin-1-yl)methanone.

MS($ES^4$): m/z=223.1 $(M+H)^+$.

Prepare the following intermediate (shown in Table 5) essentially as described for (2-aminopyrimidin-5-yl)-(4-methylpiperazin-1-yl)methanone (herein referred as Intermediate M13) using the corresponding pyridine derivative instead of pyrimidine derivative.

TABLE 5

| Intermediate | Compound | Structure | Physical Data (MS) $(M + H)^+$ |
|---|---|---|---|
| M14 | (6-aminopyridin-3-yl)(4-methylpiperazin-1-yl)methanone | 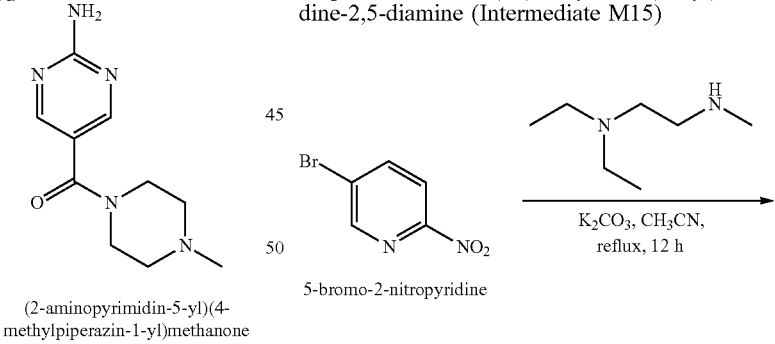 | 221.1 |

-continued (2-aminopyrimidin-5-yl)(4-methylpiperazin-1-yl)methanone

Preparation 15: $N^5$-(2-(diethylamino)ethyl)-$N^5$-methylpyridine-2,5-diamine (Intermediate M15)

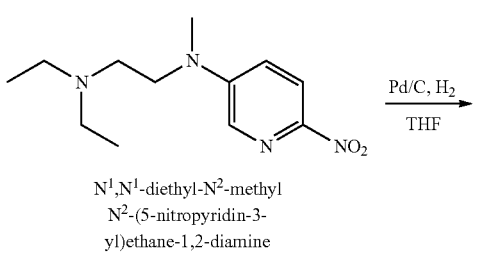

5-bromo-2-nitropyridine $N^1,N^1$-diethyl-$N^2$-methyl $N^2$-(5-nitropyridin-3-yl)ethane-1,2-diamine Add Oxone (1.810 g) to a mixture of compound MH2-12 (0.315 g) in acetone (10 mL) and water (3 mL) with stirring for 2 hrs at RT. Add water (20 mL), extract with DCM (25 mL×3), the combined organic phase dried over anhydrous $Na_2SO_4$, concentrated to give 0.290 g of compound MN8-01.

Add HATU (0.488 g) and DIEA (0.221 g) successively to a solution of compound MH8-01 (0.290 g) in DCM (10 mL) with stirring for 1 h at RT, the solution is reacted for 2 hrs after adding 1-Methylpiperazine (0.105 g) at RT. Add water

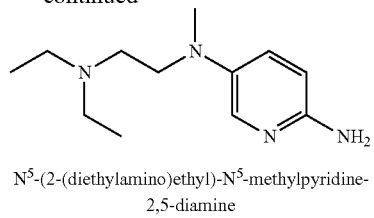

N⁵-(2-(diethylamino)ethyl)-N⁵-methylpyridine-
2,5-diamine

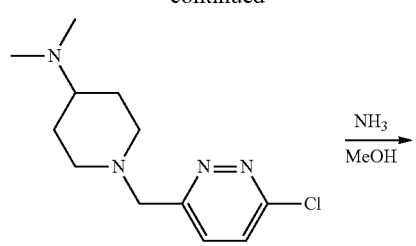

1-((6-chloropyridazin-3-
yl)methyl)-N,N-
dimethylpiperidin-4-amine $\xrightarrow{NH_3}{MeOH}$

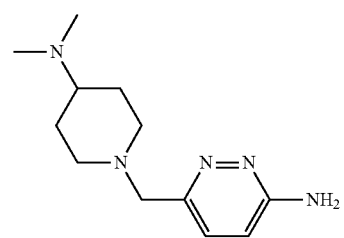

6-((4-(dimethylamino)piperidin-1-
yl)methyl)pyridazin-3-amine

Add N,N-Diethyl-N'-methylethylenediamine (0305 g) and K₂CO; (0.679 g) successively to a solution of 2-Nitro-5-bromopyridine (0.500 g) in acetonitrile (10 mL). Let the reaction stir at 82° C. for 15 hrs in an oil bath. Add water (50 mL), extract with DCM (80 mL×3), the combined organic phase was dried over anhydrous Na₂SO₄, concentrated and purified by column chromatography (DCM/MeOH=10/1) to give 0.400 g of 1-methyl-4-(6-nitropyridin-3-yl)-piperazine.

Add Pd/C (0.040 g) to a solution of 1-methyl-4-(6-nitropyridin-3-yl)piperazine in THF (15 mL) with stirring for 2 hrs at RT under hydrogen gas. The filtrate was collected by filtration and then concentrated to give 0.350 g of N⁵-(2-(diethylamino)ethyl)-N⁵-methylpyridine-2,5-diamine.

MS(ES⁺): m/z=223.2 (M+H)⁺.

Prepare the following intermediate (shown in Table 6) essentially as described for N⁵-(2-(diethylamino)ethyl)-N⁵-methylpyridine-2,5-diamine (herein referred as Intermediate M15) using N¹,N¹-diethyl-N²,N²-dimethylethane-1,2-diamine instead of N,N-Diethyl-N'-methylethylenediamine.

Add trichloroisocyanuric acid (0.189 g) to a solution of 3-Choro-6-methylpyridazine (0.208 g) in CHCl₃ (10 mL), heat to 60° C. for 12 hrs in an oil bath. Cool to room temperature, the filtrate was collected by filtration, concen-

TABLE 6

| Intermediate | Compound | Structure | Physical Data (MS) (M + H)⁺ |
|---|---|---|---|
| M16 | N⁵-(2-(diethylamino)ethyl)-N⁵-methylpyridine-2,5-diamine | 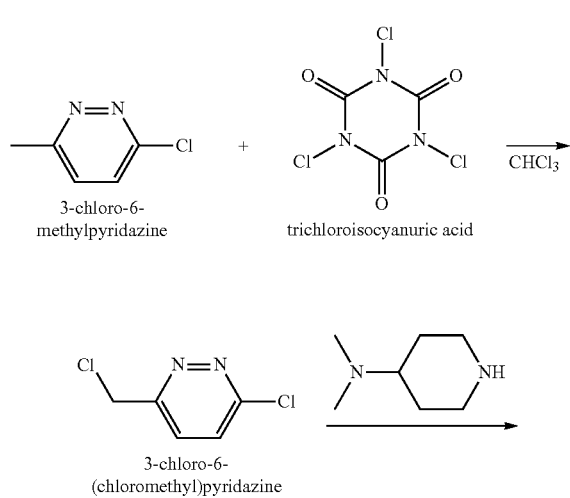 | 223.2 |

Preparation 17: 6-((4-(dimethylamino)piperidin-1-yl)methyl)pyridazin-3-amine (Intermediate M17)

trated and purified by column chromatography (PE/EA:=10/1) to give 0.201 g of 3-chloro-6-(chloromethyl)pyridazine.

Add K₂CO₃ (0.578 g), KI (0.070 g) and N,N-Dimethylpiperidin-4-amine (0.322 g) successively to a solution of 3-chloro-6-(chloromethyl)pyridazine (0.340 g) in DMF (15 mL), heat to 50° C. for 1 h in an oil bath. Cool to room temperature, add DCM (50 mL), wash combined organic layers with saturated NaCl solution and dried over anhydrous Na₂SO₄, concentrated and purified by column chromatography (DCM/MeO-1=10/1) to give 0.370 g of 1-((6-chloropyridazin-3-yl)methyl)-N,N-dimethylpiperidin-4-amine.

Add MeOH (20 mL) to a 100 mL sealed tube under ammonia at −78° C., then add 1-((6-chloropyridazin-3-yl)methyl)-N,N-dimethylpiperidin-4-amine (0.370 g) and cuprous oxide (0.532 g) successively until the volume of solution rising to 30 mL. Remove the outside bath, warn to room temperature naturally, then heat to 70° C. and react for 12 hrs. The filtrate was collected by filtration, concentrated and purified by column chromatography (DCM/MeOH=15/1) to give 0.230 g of 6-((4-(dimethylamino)piperidin-1-yl)methyl)pyridazin-3-amine. MS(ES⁺): m/z=236.2 (M+H)⁺.

Prepare the following intermediate (shown in Table 7) essentially as described for 6-((4-(dimethylamino)piperidin-1-yl)methyl)pyridazin-3-amine (herein referred as Intermediate M17) using piperazine derivative instead of piperidin derivative.

TABLE 7

| Intermediate | Compound | Structure | Physical Data (MS) (M + H)+ |
|---|---|---|---|
| M18 | 6-(4-methylpiperazin-1-yl)pyridazin-3-amine | 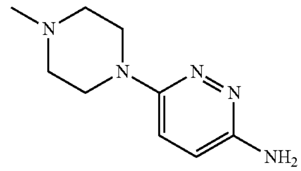 | 194.1 |

Example 1: Synthesis of Compound 1

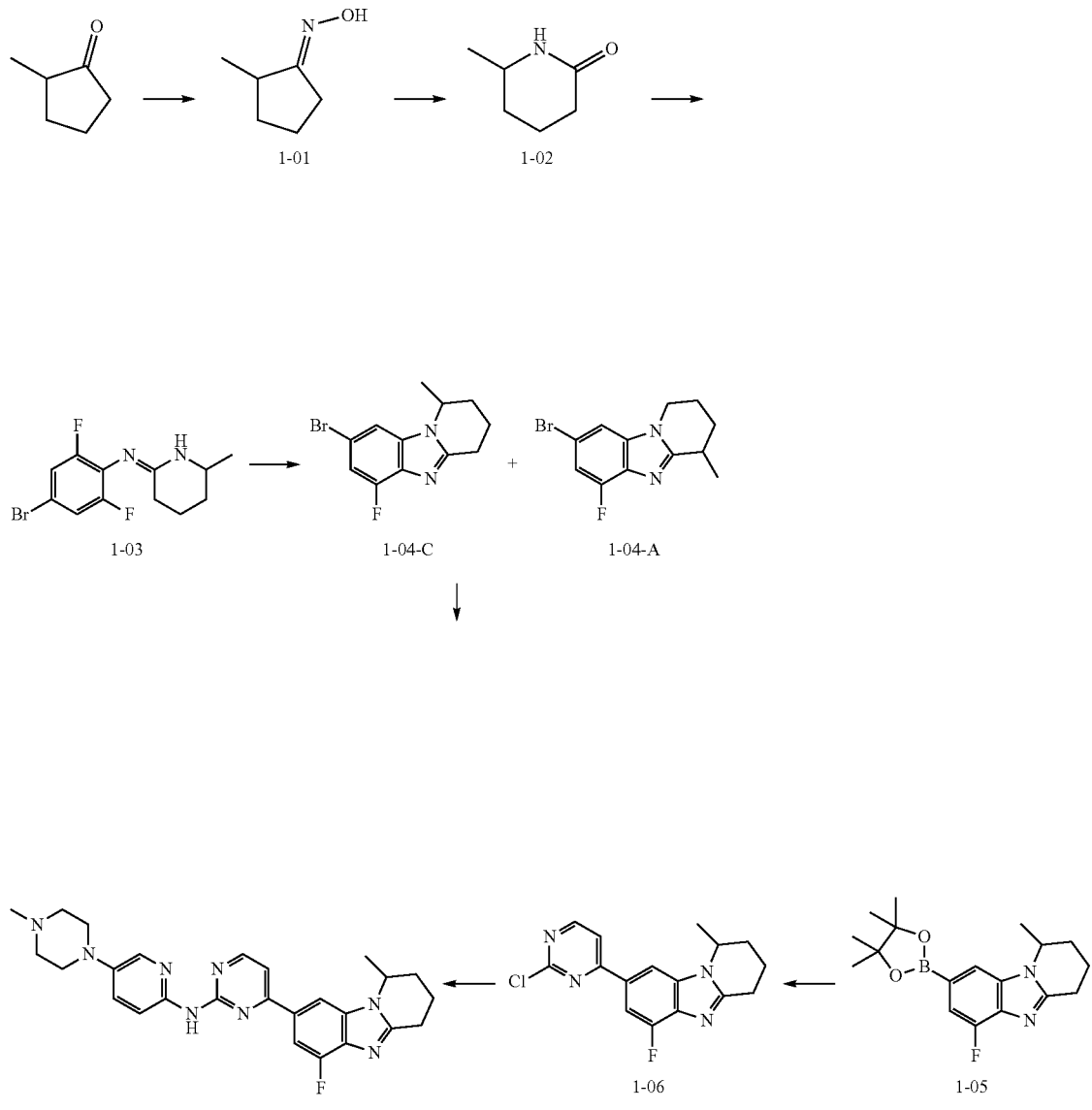

1. Compound 1-01

A mixture of 2-Methylcyclopentanone (5.200 g), Hydroxylamine hydrochloride (9.200 g) and Triethylamine (16.080 g) in anhydrous ethanol (70 mL) was stirred at 85° C. overnight in an oil bath. Then, the reaction solution was concentrated; the residue was washed with EA. The filtrate was collected by filtration and then concentrated to give 5.820 g of crude compound 1-01.

2. Compound 1-02

The crude compound 1-01 (5.820 g) was dissolved in sulfuric acid solution (con-$H_2SO_4$:$H_2O$=20 mL: 5 mL), the resulting mixture was stirred at 90° C. in an oil bath for 90 min, water (10 mL) was added, then adjusted pH to 8-9 with $Na_2CO_3$, the resulting aqueous solution was extracted with DCM (20 mL×5), the combined organic phase was dried over anhydrous $Na_2SO_4$, concentrated under reduced pressure to give 4.110 g of crude compound 1-02.

3. Compound 1-03

A mixture of crude Compound 1-02 (4.110 g) and 4-bromo-2,6-difluoroaniline (3.780 g) in methylbenzene (40 mL) was added $POCl_3$ (4.180 g) and was heated in an oil bath, TEA (2.770 g) was added when the temperature was raised to 110° C., the resulting mixture was reacting at 110° C. for 20 min. A part of methylbenzene was removed, then adjusted pH to 8~9 with $Na_2CO_3$, extracted with EA, the combined organic phase was washed with saturated NaCl solution and dried over anhydrous $Na_2SO_4$, concentrated under reduced pressure to give 6.550 g crude Compound 1-03.

4. Compound 1-04

A mixture of crude Compound 1-03 (6.100 g) and potassium tert-butoxide (4.520 g) in DMF (60 mL) was stirred at 100° C. for 20 min in an oil bath and then extracted with 300 mL EA, the combined organic phase was washed with saturated NaCl solution (120 mL×3) and dried over anhydrous $Na_2SO_4$, concentrated and then purified by column chromatography (PE/EA=1/5) to give 0.705 g of compound 1-04-A, and 1.500 g of crude compound 1-04-C.

5. Compound 1-05

A mixture of crude compound 1-04-C (0.957 g), Bis(pinacolato)diboron (1.290 g), tricyclohexyl phosphine (0.047 g), Palladium acetate (0.038 g) in DMSO (20 mL) was stirred under nitrogen for 1 h at 90° C. in an oil bath. The resulting mixture was extracted with EA (60 mL), the combined organic phase was washed with saturated NaCl solution (30 mL×3) and dried over anhydrous $Na_2SO_4$, concentrated under reduced pressure to give 2.290 g crude Compound 1-05.

6. Compound 1-06

A mixture of crude compound 1-05 (2.290 g), 2,4-Dichloropyrimidine (0.755 g), $K_2CO_3$ (1.400 g) and Pd(dppf)$Cl_2$.DCM (0.138 g) in 1,4-dioxane (30 mL) and water (3 mL) was stirred under nitrogen for 2 h at 60° C. in an oil bath. The resulting mixture was extracted with EA (30 mL×2), the combined organic phase was washed with saturated NaCl solution (30 mL×1) and dried over anhydrous $Na_2SO_4$, concentrated and then purified by column chromatography (PE/EA=1/1) to give 0.927 g of Compound 1-06.

7. Compound 1

A mixture of compound 1-06 (0.400 g), intermediate M1 (0.291 g), $Cs_2CO_3$ (0.822 g), Xanphos (0.017 g) and $Pd_2(dba)_3$ (0.027 g) in 1,4-dioxane (12 mL) was stirred under nitrogen gas for 1 h at 110° C. in an oil bath, continued to react under microwave for 0.5 h at 110'C. The resulting mixture was added water (10 mL), then extracted with DCM (20 mL×3), the combined organic phase was washed with saturated NaCl solution (30 mL×1) and dried over anhydrous $Na_2SO_4$, concentrated and then purified by column chromatography (DCM/MeOH=20/1), the solid was washed with methyl tert butyl ether (10 mL) and n-hexane (10 mL) to give 290 mg of Compound 1.

MS(ES$^+$): m/z=473.2 (M+H)$^+$.

H-NMR (CDCl$_3$): δ8.498-8.511 (d, 1H, CH), 8.373-8.396 (d, 1H, CH), 8.167 (s, 1H, CH), 8.040-8.047 (d, 1H, CH), 7.963 (s, 1H, CH), 7.631-7.660 (d, 1H, CH), 7.346-7.660 (dd, 1H, CH), 7.177-7.190 (d, 1H, CH), 4.687-4.719 (m, 1H, CH$_2$), 3.190-3.10 (m, 4H, CH$_2$), 2.651-2.675 (m, 4H, CH$_2$), 2.999-3.024 (m, 1H, CH$_2$), 2.403 (s, 3H, CH$_3$), 2.337-2.356 (m, 1H, CH$_2$, 2.267-2.357 (m, 1H, CH$_2$), 2.219-2.248 (m, 1H, CH$_2$), 2.010-2.056 (m, 2H, CH$_2$), 1.602-1.618 (d, 3H, CH$_3$).

Example 1-1 Chiral Separation of Compound 1-06

Techniques useful for the separation of isomers, e.g., enantiomers are within skill of the art and are described in Eliel, E. L.; Wilen, S. H.; Mander, L. N. *stereochemistry of Organic Compounds*, Wiley Interscience, NY, 1994. For example compound 1, 2 or 15 can be resolved to a high enantiomeric excess (e.g., 60%, 70%, 80%, 90%, 95%, 99% or greater) via high performance liquid chromatography using a chiral column. In some embodiments, the crude compound 1-06 of the Example 1 is purified directly on a chiral column to provide enantiomerically enriched compound.

Chiral HPLC Conditions:

| Column | CHIRALPAK IE |
| --- | --- |
| Column size | 2 cm * 25 cm |
| Injection | 0.7 mL |
| Mobile phase | Hex: EtOH = 65:35(v/v) |
| Flow rate | 19 mL/min |
| Wave length | UV 220 nm |
| Temperature | 35° C. |
| Sample solution | 80 mg/mL in Mobile phase |
| Prep- HPLC equipment | Prep- Gilson-HPLC |
| Sample name | Compound 1-06 |

Example 1-2 Synthesis of Compound 1a and Compound 1b

The crude Compound 1-06 is purified by chiral column under the above conditions to give Compound 1-06-A and Compound 1-06-B.

Prepare Compound 1a and Compound 1b essentially as described for step 7 of Example 1 using Compound 1-06-A and Compound 1-06-B respectively.

Furthermore, Optical rotations were measured 3 times for each compound shown as below on a Rudolf polarimeter.

Conditions:

| Polarimeter tube length | 100 mm |
| --- | --- |
| Temperature | 20° C. |
| Sample solution | 3.0 mg/mL in EtOH |
| Sample name | Compound 1a and Compound 1b |

Results:

| | (1st) (°) | (2nd) (°) | (3rd) (°) | Average (°) |
|---|---|---|---|---|
| Compound 1a | 30.357 | 30.711 | 29.906 | 30.325 |
| Compound 1b | −35.430 | −35.453 | −35.298 | −35.394 |

Example 2: Synthesis of Compound 2

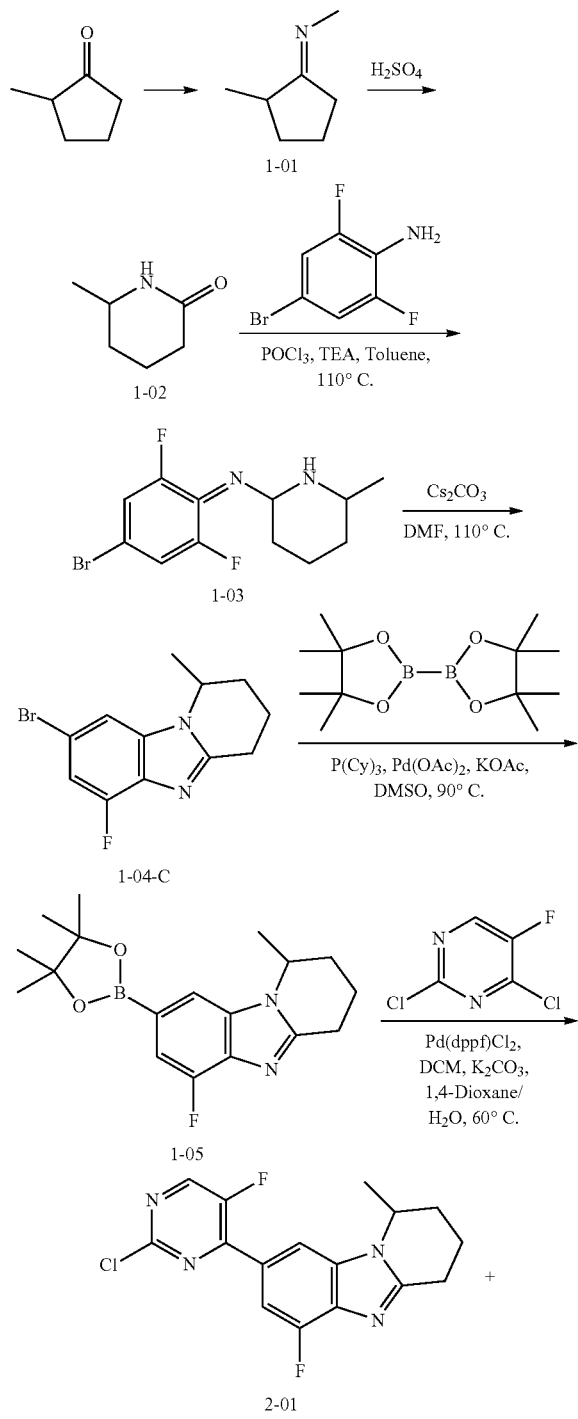

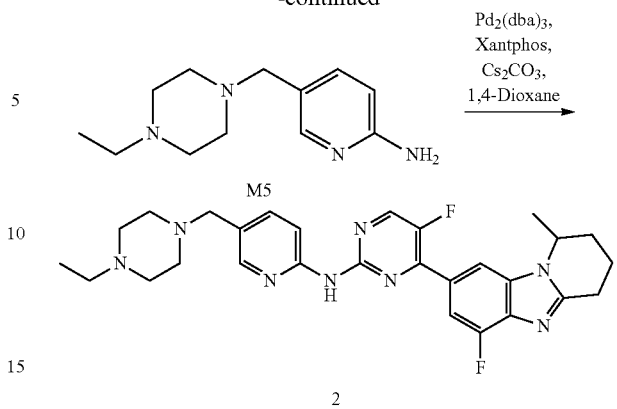

1. Compound 1-01

A mixture of 2-Methylcyclopentanone (5.200 g), Hydroxylamine hydrochloride (9.200 g) and Triethylamine (16.080 g) in anhydrous ethanol (70 mL) was stirred at 85° C. overnight in an oil bath. Then, the reaction solution was concentrated; the residue was washed with EA. The filtrate was collected by filtration and then concentrated to give 5.820 g of crude compound 1-01.

2, Compound 1-02

The crude compound 1-01 (5.820 g) was dissolved in sulfuric acid solution (con-$H_2SO_4$:$H_2O$=20 mL: 5 mL), the resulting mixture was stirred at 90° C. in an oil bath for 90 min, water (10 mL) was added, then adjusted pH to 8-9 with $Na_2CO_3$, the resulting aqueous solution was extracted with DCM (20 mL×5), the combined organic phase was dried over anhydrous $Na_2SO_4$, concentrated under reduced pressure to give 4.110 g of crude compound 1-02.

3. Compound 1-03

A mixture of crude Compound 1-02 (4.110 g) and 4-bromo-2,6-difluoroaniline (3.780 g) in methylbenzene (40 mL) was added $POCl_3$ (4.180 g) and was heated in an oil bath, TEA (2.770 g) was added when the temperature was raised to 110° C., the resulting mixture was reacting at 110° C. for 20 min. A part of methylbenzene was removed, then adjusted pH to 8~-9 with $Na_2CO_3$, extracted with EA, the combined organic phase was washed with saturated NaCl solution and dried over anhydrous $Na_2SO_4$, concentrated under reduced pressure to give 6.550 g crude Compound 1-03.

4. Compound 1-04

A mixture of crude Compound 1-03 (6.100 g) and potassium tert-butoxide (4.520 g) in DMF (60 mL) was stirred at 100° C. for 20 min in an oil bath and then extracted with 300 mL EA, the combined organic phase was washed with saturated NaCl solution (120 mL×3) and dried over anhydrous $Na_2SO_4$, concentrated and then purified by column chromatography (PE/EA=1/5) to give 0.705 g of compound 1-04-A, and 1.500 g of crude compound 1-04-C.

5. Compound 1-05

A mixture of crude compound 1-04-C (0.200 g), Bis (pinacolato)diboron (0.270 g), tricyclohexyl phosphine (0.039 g), Palladium acetate (0.031 g) in DMSO (5 mL) was stirred under nitrogen for 1 h at 90° C. in an oil bath. The resulting mixture was extracted with EA (50 mL), the combined organic phase was washed with saturated NaCl solution (20 mL×3) and dried over anhydrous $Na_2SO_4$, concentrated under reduced pressure to give 0.398 g crude Compound 1-05.

6. Compound 2-01

A mixture of crude compound 1-05 (0.398 g), 2,4-Dichloropyrimidine (0.304 g), $K_2CO_3$ (0.502 g) and Pd(dppf)$Cl_2$.DCM (0.050 g) in 1,4-dioxane (10 mL) and water (1 mL) was stirred under nitrogen for 80 min at 60° (in an oil bath. The resulting mixture was added water (10 mL) and then extracted with EA (20 mL×2), the combined organic phase was washed with saturated NaCl solution (20 mL×1) and dried over anhydrous $Na_2SO_4$, concentrated and then purified by column chromatography (PE/EA=1/1) to give 0.165 g of Compound 2-01.

7. Compound 2

A mixture of compound 2-01 (0.030 g), Intermediate M5 (0.025 g), $Cs_2CO_3$ (0.067 g), Xanphos (0.005 g) and $Pd_2$(dba)$_3$ (0.005 g) in 1,4-dioxane (2 mL) was stirred under nitrogen gas for 3.5 h at 110° C. in an oil bath. The resulting mixture was added 20 mL of mixture solvent (DCM/MeOH=10/1), then filtered, concentrated and purified by column chromatography (DCM/MeOH=8/l), the solid was washed with 1,4-dioxane (5 mL) to give 0.024 g of Compound 2.

MS(ES$^+$): m/z=519.3 (M+H)$^+$.

H-NMR (CDCl$_3$): δ 8.587 (s, 1H, NH), 8.448-8.457 (d, 1H, CH), 8.383-8.405 (d, 1H, CH), 8.280-8.286 (d, 1H, CH), 8.009-8.013 (d, 1H, CH), 7.804-7.837 (dd, 1H, CH), 7.6867.714 (dd, 1H, CH), 4.681-4.728 (m, 1H, CH), 3.532 (s, 2H, CH$_2$), 3.189-3.256 (m, 1H, CH$_2$), 3.008-3.091 (m, 1H, CH$_2$), 2.654 (s, 8H, CH$_2$), 2.571-2.608 (m, 2H, CH$_2$), 2.226-2.299 (m, 1H, CH$_2$), 2.111-2.15 (m, 1H, CH$_2$), 2.012-2.053 (m, 2H, CH$_2$), 1.596-1.612 (d, 3H, CH$_3$), 1.174-1.210 (t, 3H, CH$_3$).

Example 2-1 Chiral Separation of Compound 2-01

In this embodiment, the crude compound 2-01 of the Example 2 is purified directly on a chiral column to provide compound 2-01-A and compound 2-01-B under the following conditions.

Chiral HPLC Conditions:

| Column | CHIRALPAK AD-H |
|---|---|
| Column size | 2 cm * 25 cm, 5 μm |
| Injection | 1.0 mL |
| Mobile phase | Hex: IPA = 90:10(v/v) |
| Flow rate | 20 mL/min |
| Wave length | UV 220 nm |
| Temperature | 25° C. |
| Sample solution | 25.9 mg/mL in EtOH:CAN = 3:1 |
| Prep- HPLC equipment | Prep- YMC-HPLC |
| Sample name | Compound 2-01 |

Example 2-2 Synthesis of Compound 2a and Compound 2b

The crude compound 2-01 is purified by chiral column under the above conditions to give Compound 2-01-A and Compound 2-01-B.

Prepare Compound 2a and Compound 2b essentially as described for step 7 of Example 2 using Compound 2-01-A and Compound 2-01-B respectively.

Furthermore, Optical rotations were measured 3 times for each compound shown as below on a Rudolf polarimeter.

Conditions:

| Polarimeter tube length | 100 mm |
|---|---|
| Temperature | 20° C. |
| Sample solution | 4.0 mg/mL in DCM |
| Sample name | Compound 2a and Compound 2b |

Results:

| | 1$^{st}$ (°) | 2$^{nd}$ (°) | 3$^{rd}$ (°) | Average (°) |
|---|---|---|---|---|
| Compound 2a | 38.074 | 38.111 | 38.078 | 38.088 |
| Compound 2b | −32.070 | −32.134 | −31.903 | −32.036 |

Prepare the following examples (shown in Table 8) essentially as described for Example 2 using the corresponding intermediates. Wherein the two enantiomers of each compound are separated on a chiral column, then test their optical rotation respectively essentially as described for Example 2-2.

TABLE 8

| EX No. | Chemical Name | Structure | Physical Data (MS) (M + H)$^+$ | Enantiomers (optical rotation) |
|---|---|---|---|---|
| 1 | 4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine | 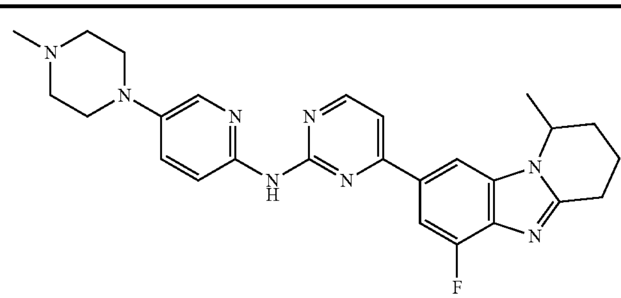 | 473.2 | 1a (+)<br>1b (−) |

TABLE 8-continued

| EX No. | Chemical Name | Structure | Physical Data (MS) (M + H)+ | Enantiomers (optical rotation) |
|---|---|---|---|---|
| 2 | N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine | 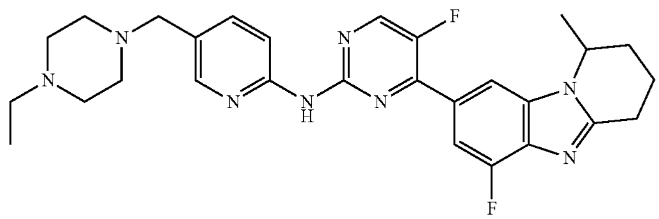 [SMILES: CCN1CCN(Cc2ccc(Nc3ncc(F)c(-c4cc(F)c5nc6n(c5c4)C(C)CCC6)n3)nc2)CC1] | 519.3 | 2a (+)<br>2b (−) |
| 3 | 5-fluoro-4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine | 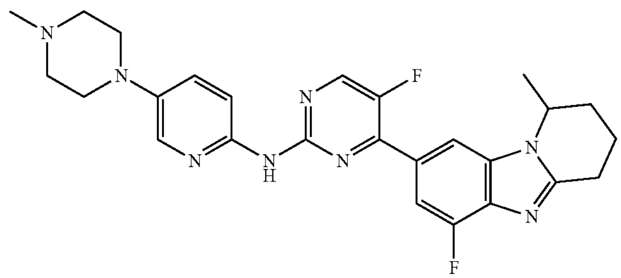 [SMILES: CC1CCCc2nc3c(F)cc(-c4nc(Nc5ccc(N6CCN(C)CC6)cn5)ncc4F)cc3n21] | 491.2 | 3a (+)<br>3b (−) |
| 4 | 5-fluoro-4-(6-fluoro-1-methyl-1,2,3,4-tetrahydrobenzo[4,5]imidazo[1,2-a]pyridin-8-yl)-N-(6-((4-methylpiperazin-1-yl)methyl)pyridin-3-yl)pyrimidin-2-amine | 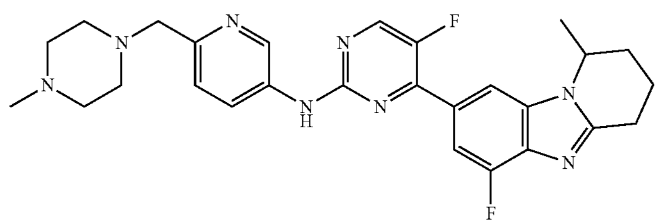 [SMILES: CC1CCCc2nc3c(F)cc(-c4nc(Nc5ccc(CN6CCN(C)CC6)nc5)ncc4F)cc3n21] | 505.3 | 4a (+)<br>4b (−) |
| 5 | 5-fluoro-4-(6-fluoro-1-methyl-1,2,3,4-tetrahydrobenzo[4,5]imidazo[1,2-a]pyridin-8-yl)-N-(5-((4-methylpiperazin-1-yl)methyl)pyrimidin-2-yl)pyrimidin-2-amine | 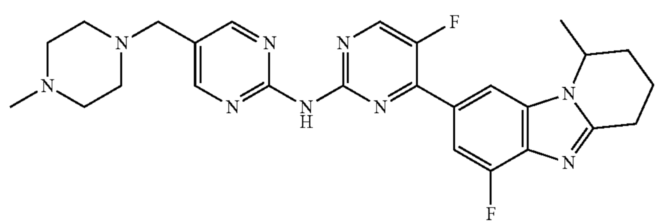 [SMILES: CC1CCCc2nc3c(F)cc(-c4nc(Nc5ncc(CN6CCN(C)CC6)cn5)ncc4F)cc3n21] | 506.3 | 5a (+)<br>5b (−) |
| 6 | N-(5-((4-(dimethylamino)piperidin-1-yl)methyl)pyrimidin-2-yl)-5-fluoro-4-(6-fluoro-1-methyl-1,2,3,4-tetrahydrobenzo[4,5]imidazo[1,2-a]pyridin-8-yl)pyrimidin-2-amine | 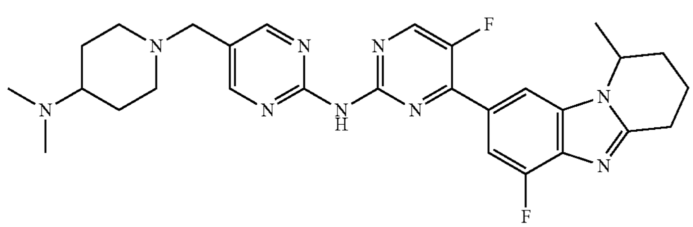 [SMILES: CC1CCCc2nc3c(F)cc(-c4nc(Nc5ncc(CN6CCC(N(C)C)CC6)cn5)ncc4F)cc3n21] | 534. | 6a (+)<br>6b (−) |
| 7 | N-(5-((4-(dimethylamino)piperidin-1-yl)methyl)pyridin-2-yl)-5-fluoro-4-(6-fluoro-1-methyl-1,2,3,4-tetrahydrobenzo[4,5]imidazi[1,2-a]pyridin-8-yl)pyrimidin-2-amine | 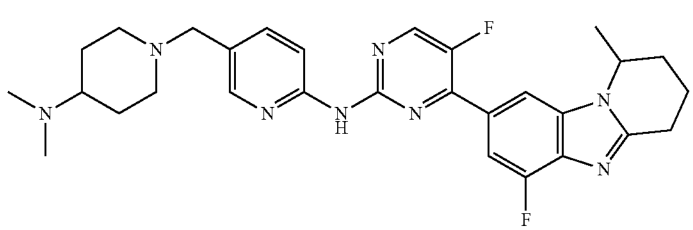 [SMILES: CC1CCCc2nc3c(F)cc(-c4nc(Nc5ccc(CN6CCC(N(C)C)CC6)cn5)ncc4F)cc3n21] | 533.3 | 7a (+)<br>7b (−) |

TABLE 8-continued

| EX No. | Chemical Name | Structure | Physical Data (MS) (M + H)+ | Enantiomers (optical rotation) |
|---|---|---|---|---|
| 8 | N-(5-(4-(dimethylamino) piperidin-1-yl)pyridin-2-yl)-5-fluoro-4-(6-fluoro-1-methyl-1,2,3,4-tetrahydrobenzo[4,5]imidazo[1,2-a] pyridin-8-yl)pyrimidin-2-amine | 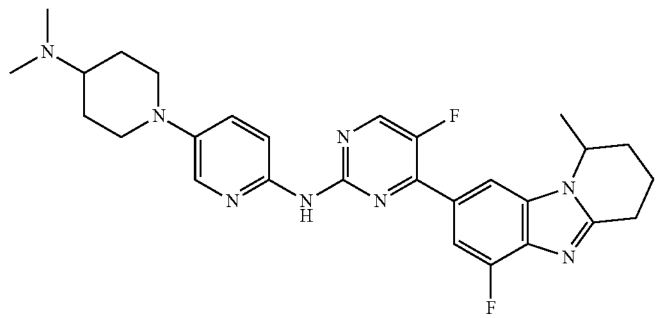 [SMILES: CC1CCCc2nc3c(F)cc(-c4nc(Nc5ccc(N6CCC(N(C)C)CC6)cn5)ncc4F)cc3n21] | 519.3 | 8a (+) 8b (−) |
| 9 | (2-((5-fluoro-4-(6-fluoro-1-methyl-1,2,3,4-tetrahydrobenzo[4,5]imidazo[1,2-a]pyridin-8-yl)pyrimidin-2-yl)amino)pyrimidin-5-yl)(4-methylpiperazin-1-yl)methanone | 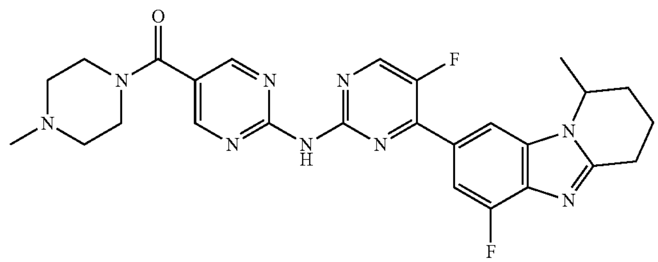 [SMILES: CC1CCCc2nc3c(F)cc(-c4nc(Nc5ncc(C(=O)N6CCN(C)CC6)cn5)ncc4F)cc3n21] | 520.2 | 9a (+) 9b (−) |
| 10 | (6-((5-fluoro-4-(6-fluoro-1-methyl-1,2,3,4-tetrahydrobenzo[4,5]imidazo[1,2-a]pyridin-8-yl)pyrimidin-2-yl)amino)pyridin-3-yl)(4-methylpiperazin-1-yl)methanone | 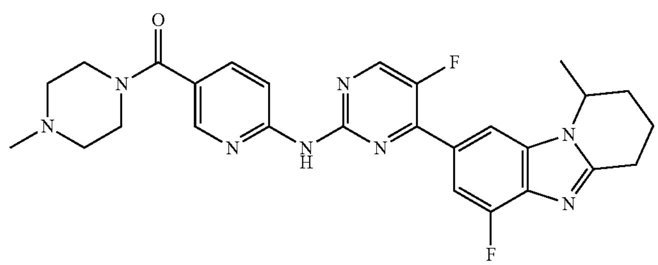 [SMILES: CC1CCCc2nc3c(F)cc(-c4nc(Nc5ccc(C(=O)N6CCN(C)CC6)cn5)ncc4F)cc3n21] | 519.2 | 10a (+) 10b (−) |
| 11 | N5-(2-(diethylamino)ethyl)-N2-(5-fluoro-4-(6-fluoro-1-methyl-1,2,3,4-tetrahydrobenzo[4,5]imidazo[1,2-a]pyridin-8-yl)pyrimidin-2-yl)-N5-methylpyridine-2,5-diamine | 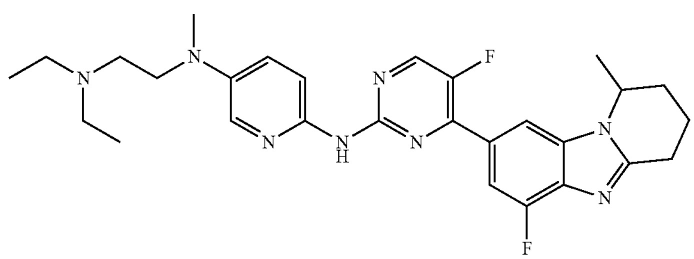 [SMILES: CCN(CC)CCN(C)c1ccc(Nc2ncc(F)c(-c3cc(F)c4nc5n(c4c3)C(C)CCC5)n2)nc1] | 521.3 | 11a (+) 11b (−) |
| 12 | N-(5-((4-ethylpiperazin-1-yl)methyl)pyridin-2-yl)-4-(6-fluoro-1-methyl-1,2,3,4,4a,5-hexahydrobenzo[4,5]imidazo[1,2-a]pyridin-8-yl)-5-(trifluoromethyl)pyrimidin-2-amine | 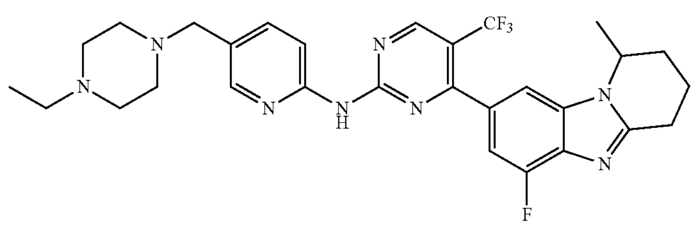 [SMILES: CCN1CCN(Cc2ccc(Nc3ncc(C(F)(F)F)c(-c4cc(F)c5nc6n(c5c4)C(C)CCC6)n3)nc2)CC1] | 571.3 | 12a (+) 12b (−) |
| 13 | N-(5((4-ethylpiperazin-1-yl)methyl)pyridin-2-yl)-4-(6-fluoro-1-methyl-1,2,3,4,4a,5-hexahydrobenzo[4,5]imidazo[1,2-a]pyridin-8-yl)-5-methylpyrimidin-2-amine | 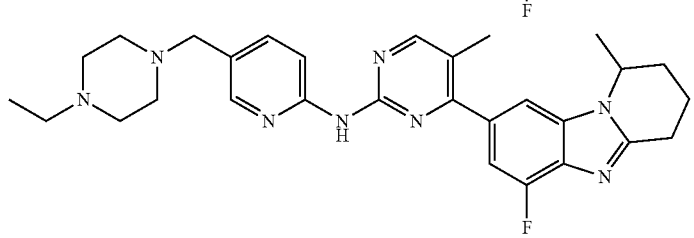 | 517.3 | 13a (+) 13b (−) |

TABLE 8-continued

| EX No. | Chemical Name | Structure | Physical Data (MS) (M + H)+ | Enantiomers (optical rotation) |
|---|---|---|---|---|
| 14 | 5-chloro-N-(5-((4-ethylpiperazin-1-yl)methyl)pyridin-2-yl)-4-(6-fluoro-1-methyl-1,2,3,4-tetrahydrobenzo[4,5]imidazo[1,2-a]pyridin-8-yl)pyrimidin-2-amine | 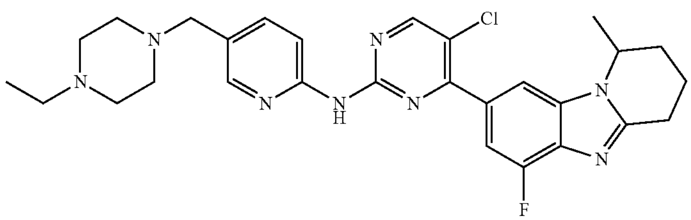 [SMILES: CCN1CCN(Cc2ccc(Nc3ncc(Cl)c(-c4cc(F)c5nc6n(c5c4)C(C)CCC6)n3)nc2)CC1] | 535.2 | 14a (+) 14b (−) |

Example 15: Synthesis of Compound 15b

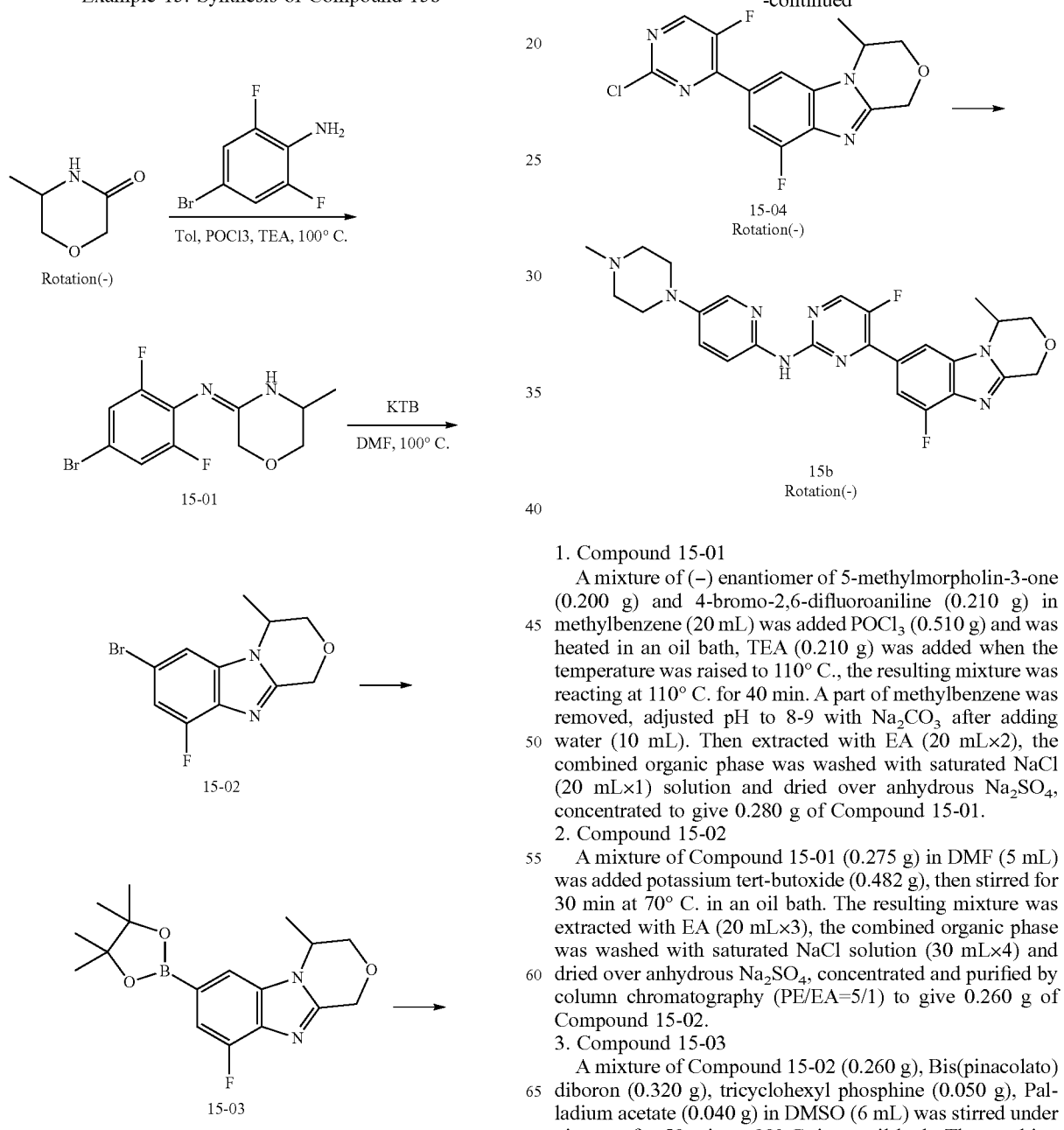

1. Compound 15-01

A mixture of (−) enantiomer of 5-methylmorpholin-3-one (0.200 g) and 4-bromo-2,6-difluoroaniline (0.210 g) in methylbenzene (20 mL) was added POCl₃ (0.510 g) and was heated in an oil bath, TEA (0.210 g) was added when the temperature was raised to 110° C., the resulting mixture was reacting at 110° C. for 40 min. A part of methylbenzene was removed, adjusted pH to 8-9 with Na₂CO₃ after adding water (10 mL). Then extracted with EA (20 mL×2), the combined organic phase was washed with saturated NaCl (20 mL×1) solution and dried over anhydrous Na₂SO₄, concentrated to give 0.280 g of Compound 15-01.

2. Compound 15-02

A mixture of Compound 15-01 (0.275 g) in DMF (5 mL) was added potassium tert-butoxide (0.482 g), then stirred for 30 min at 70° C. in an oil bath. The resulting mixture was extracted with EA (20 mL×3), the combined organic phase was washed with saturated NaCl solution (30 mL×4) and dried over anhydrous Na₂SO₄, concentrated and purified by column chromatography (PE/EA=5/1) to give 0.260 g of Compound 15-02.

3. Compound 15-03

A mixture of Compound 15-02 (0.260 g), Bis(pinacolato)diboron (0.320 g), tricyclohexyl phosphine (0.050 g), Palladium acetate (0.040 g) in DMSO (6 mL) was stirred under nitrogen for 50 min at 90° C. in an oil bath. The resulting mixture was extracted with EA (20 mL×2), the combined organic phase was washed with saturated NaCl solution (10 mL×3) and dried over anhydrous $Na_2SO_4$, concentrated to give 0.258 g of Compound 15-03.

4. Compound 15-04

A mixture of Compound 15-03 (0.120 g), 2,4-Dichloro-5-fluoropyrimidine (0.060 g), $K_2CO_3$ (0.099 g) and Pd(dppf)$Cl_2$.DCM (0.012 g) in 1,4-dioxane (10 mL) and water (1 mL) was stirred under nitrogen for 1 h at 60° C. in an oil bath. The resulting mixture was extracted with EA (20 mL×2), the combined organic phase was washed with saturated NaCl solution (20 mL×1) and dried over anhydrous $Na_2SO_4$, concentrated and then purified by preparative HPLC (DCM/MeOH=30/1) to give 0.052 g of (−) enantiomer of Compound 15-04.

5. Compound 15b (−) enantiomer of Compound 15-04 (20 mg), intermediate M1 (0.017 g), $Cs_2CO_3$ (0.056 g), Xanphos (0.005 g) and $Pd_2(dba)_3$ (0.005 g) in 1,4-dioxane (2 mL) was reacted under microwave at 110° C. for 1.5 hrs through nitrogen stream. The resulting mixture was added 20 mL of mixture solvents (DCM/MeOH=10/1), the filtrate was collected by filtration and then concentrated, purified by preparative HPLC (DCM/MeOH=20/1), the resulting solid was washed with n-hexane (10 mL) to give 0.014 g of Compound 15b.

MS(ES$^+$): m/z=493.2 (M+H)$^+$.

H-NMR (CDCl3): δ 8.409-8.418 (d, 1H, CH), 8.211-8.288 (m, 2H, CH), 8.070-8.077 (d, 1H, CH), 8.019-8.023 (d, 1H, CH), 7.833-7.868 (n, 1H, CH), 5.118-5.158 (d, 1H, CH2), 4.912-5.002 (d, 1, CH2), 4.522-4.584 (m, 1H, CH), 4.111-4.168 (m, 1H, CH2), 4.039-4.075 (m, 1H, CH2), 3.249-3.275 (m, 4H, CH2), 2.724-2.748 (m, 4H, CH2), 2.462 (s, 3, CH3), 1.662-1.678 (d, 3H, CH3).

Example 15-1 Synthesis of Compound 15a and Compound 15

Compound 15a and Compound 15b are enantiomers. Prepare Compound 15a essentially as described for Example 15 using (+) enantiomer of 5-methylmorpholin-3-one as starting material.

In another embodiment, crude 5-methylmorpholin-3-one is used as starting material; the crude compound 15 including Compound 15a and Compound 15b will be obtained in the end.

Furthermore, Optical rotations were measured 3 times for each compound shown as below on a Rudolf polarimeter. Conditions:

| Polarimeter tube length | 100 mm |
|---|---|
| Temperature | 20° C. |
| Sample solution | 4.6 mg/mL in DCM/MeOH(1:1) |
| Sample name | Compound 15a and Compound 15b |

Results:

| | 1$^{st}$ (°) | 2$^{nd}$ (°) | 3$^{rd}$ (°) | Average (°) |
|---|---|---|---|---|
| Compound 15a | 32.859 | 32.818 | 32.809 | 32.829 |
| Compound 15b | −28.979 | −28.840 | −28.967 | −28.979 |

Prepare the following examples (shown in Table 9) essentially as described for Example 15 using the corresponding intermediates, and using (+) and/or (−) enantiomer of 5-methylmorpholin-3-one as starting material. Their optical rotations were essentially tested as described for Example 15-1.

TABLE 9

| EX No. | Chemical Name | Structure | Physical Data (MS) (M + H)$^+$ | Enantiomers (optical rotation) |
|---|---|---|---|---|
| 15 | 5-fluoro-4-(9-fluoro-4-methyl-3,4-dihydro-1H-benzo[4,5]imidazo[2,1-c][1,4]oxazin-7-yl)-N-(5-(4-methylpiperazin-1-yl)pyridin-2-yl)pyrimidin-2-amine | 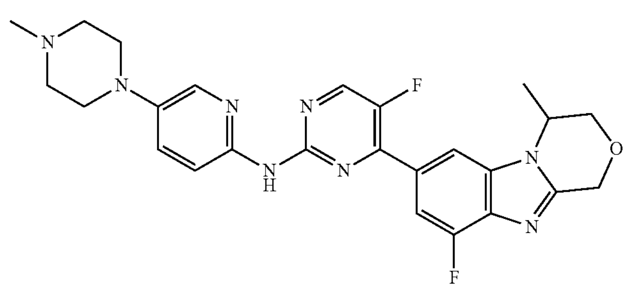 [SMILES: CC1COCc2nc3c(F)cc(-c4nc(Nc5ccc(N6CCN(C)CC6)cn5)ncc4F)cc3n21] | 493.2 | 15a (+) 15b (−) |
| 16 | N-(5-((4-ethylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine | 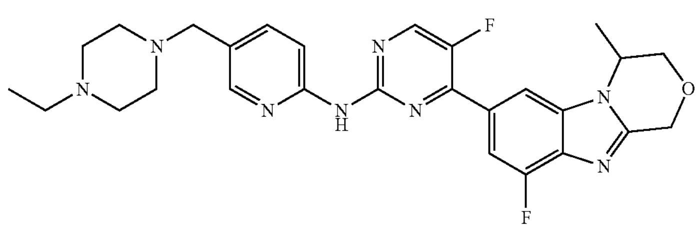 [SMILES: CCN1CCN(Cc2ccc(Nc3ncc(F)c(-c4cc(F)c5nc6n(c5c4)C(C)COC6)n3)nc2)CC1] | 521.3 | 16a (+) 16b (−) |

TABLE 9-continued

| EX No. | Chemical Name | Structure | Physical Data (MS) (M + H)+ | Enantiomers (optical rotation) |
|---|---|---|---|---|
| 17 | N-5-(4-(dimethylamino)piperidin-1-yl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine | 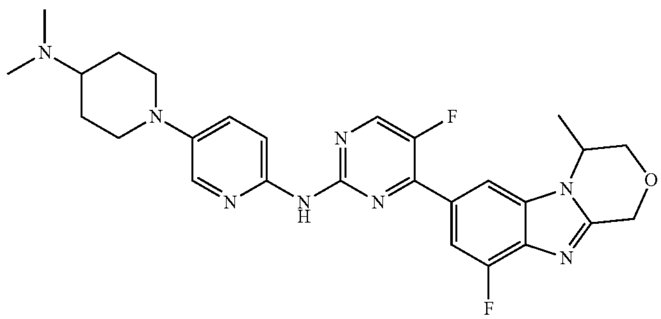 [SMILES: CC1COCc2nc3c(F)cc(-c4nc(Nc5ccc(N6CCC(N(C)C)CC6)cn5)ncc4F)cc3n21] | 521.3 | 17a (+) 17b (−) |
| 18 | N-(5-((4-(dimethylamino)piperidin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine | 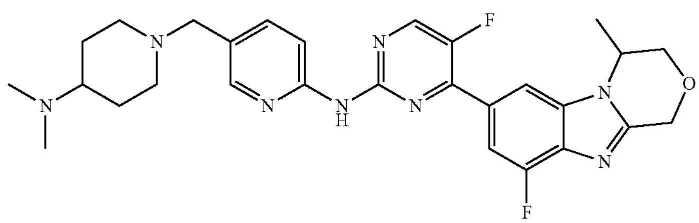 [SMILES: CC1COCc2nc3c(F)cc(-c4nc(Nc5ccc(CN6CCC(N(C)C)CC6)cn5)ncc4F)cc3n21] | 535.3 | 18a (+) 18b (−) |
| 19 | 5-fluoro-4-(9-fluoro-4-methyl-3,4-dihydro-1H-benzo[4,5]imidazo[2,1-c][1,4]oxazin-7-yl)-N-(5-(piperazin-1-yl)pyridin-2-yl)pyrimidin-2-amine | 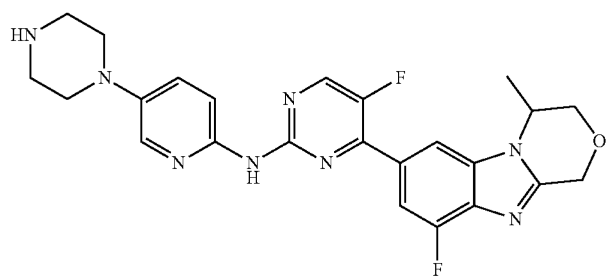 [SMILES: CC1COCc2nc3c(F)cc(-c4nc(Nc5ccc(N6CCNCC6)cn5)ncc4F)cc3n21] | 479.2 | 19a (+) 19b (−) |
| 20 | 5-fluoro-4-(9-fluoro-4-methyl-3,4-dihydro-1H-benzo[4,5]imidazo[2,1-c][1,4]oxazin-7-yl)-N-(5-(piperazin-1-ylmethyl)pyridin-2-yl)pyrimidin-2-amine | 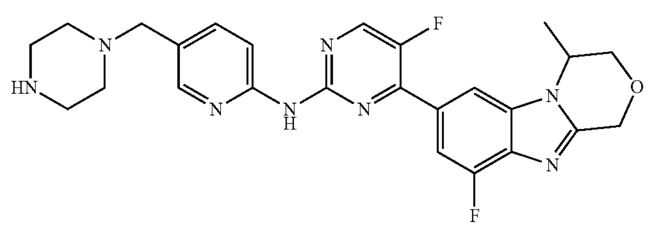 [SMILES: CC1COCc2nc3c(F)cc(-c4nc(Nc5ccc(CN6CCNCC6)cn5)ncc4F)cc3n21] | 493.2 | 20a (+) 20b (−) |
| 21 | N-(5-fluoro-4-(9-fluoro-4-methyl-3,4-dihydro-1H-benzo[4,5]imidazo[2,1-c][1,4]oxazin-7-yl)pyrimidin-2-yl)-6-(4-methylpiperazin-1-yl)pyridazin-3-amine | 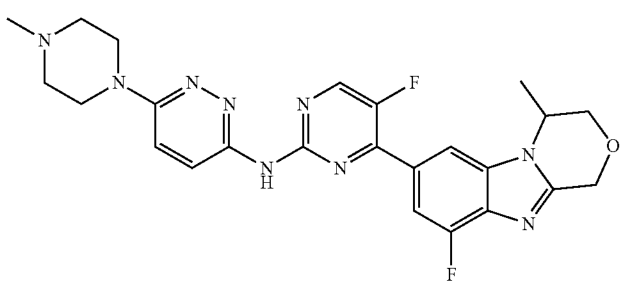 [SMILES: CC1COCc2nc3c(F)cc(-c4nc(Nc5ccc(N6CCN(C)CC6)nn5)ncc4F)cc3n21] | 494.2 | 21a (+) 21b (−) |

TABLE 9-continued

| EX No. | Chemical Name | Structure | Physical Data (MS) (M + H)+ | Enantiomers (optical rotation) |
|---|---|---|---|---|
| 22 | 6-((4-ethylpiperazin-1-yl)methyl)-N-(5-fluoro-4-(9-fluoro-4-methyl-3,4-dihydro-1H-benzo[4,5]imidazo[2,1-c][1,4]oxazin-7-yl)pyrimidin-2-yl)pyridazin-3-amine | 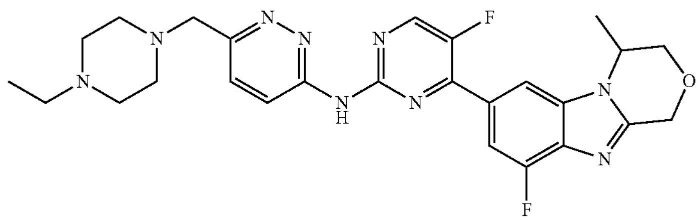 [SMILES: CCN1CCN(Cc2ccc(Nc3ncc(F)c(-c4cc(F)c5nc6n(c5c4)C(C)COC6)n3)nn2)CC1] | 522.2 | 22a (+) 22b (−) |
| 23 | (1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)pyrrolidin-3-yl)methanol | 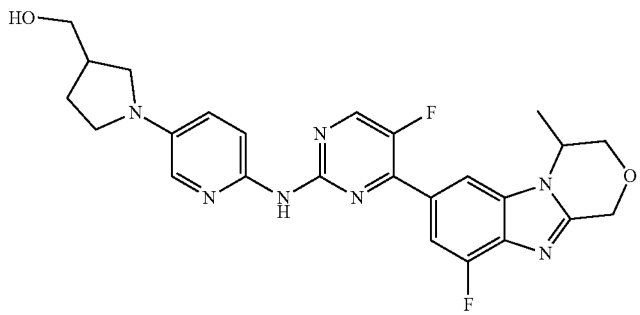 [SMILES: CC1COCc2nc3c(F)cc(-c4nc(Nc5ccc(N6CCC(CO)C6)cn5)ncc4F)cc3n21] | 494.2 | 23a (+) 23b (−) |
| 24 | (1-((6-((5-fluoro-4-(9-fluoro-4-methyl-3,4-dihydro-1H-benzo[4,5]imidaz[2,1-c][1,4]oxazin-7-yl)pyrimidin-2-yl)amino)pyridin-3-yl)methyl)pyrrolidin-3-methanol | 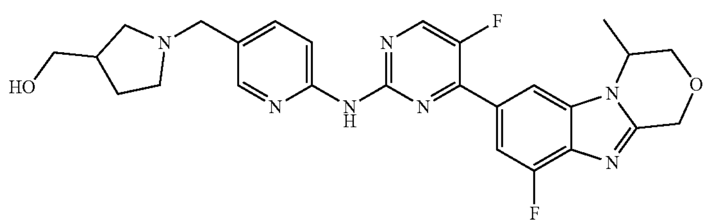 [SMILES: CC1COCc2nc3c(F)cc(-c4nc(Nc5ccc(CN6CCC(CO)C6)cn5)ncc4F)cc3n21] | 508.2 | 24a (+) 24b (−) |
| 25 | N-(5-(4-cyclopropylpiperazin-1-yl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine | 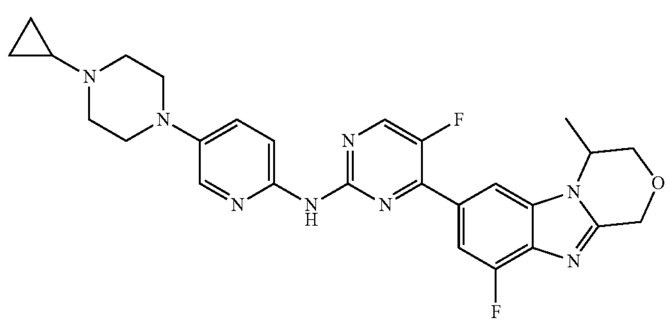 [SMILES: CC1COCc2nc3c(F)cc(-c4nc(Nc5ccc(N6CCN(C7CC7)CC6)cn5)ncc4F)cc3n21] | 519.2 | 25a (+) 25b (−) |
| 26 | N-(5-((4-cyclopropylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine | 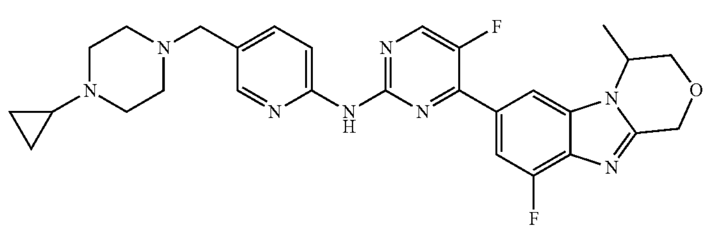 [SMILES: CC1COCc2nc3c(F)cc(-c4nc(Nc5ccc(CN6CCN(C7CC7)CC6)cn5)ncc4F)cc3n21] | 533.3 | 26a (+) 26b (−) |

TABLE 9-continued

| EX No. | Chemical Name | Structure | Physical Data (MS) (M + H)+ | Enantiomers (optical rotation) |
|---|---|---|---|---|
| 27 | 2-((1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)piperidin-4-yl)(methyl)amino)ethan-1-ol | 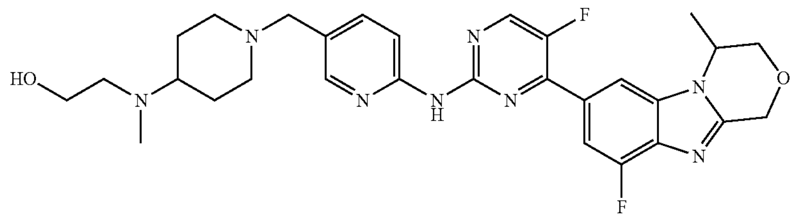 [SMILES: CC1COCc2nc3c(F)cc(-c4nc(Nc5ccc(CN6CCC(N(C)CCO)CC6)cn5)ncc4F)cc3n21] | 565.3 | 27a (+) 27b (−) |
| 28 | 1-(6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)-3-methylpyrrolidin-3-ol | 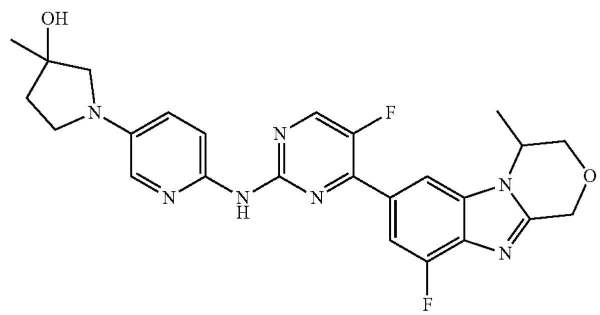 [SMILES: CC1COCc2nc3c(F)cc(-c4nc(Nc5ccc(N6CCC(C)(O)C6)cn5)ncc4F)cc3n21] | 494.2 | 28a (+) 28b (−) |
| 29 | 1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)-3-methylpyrrolidin-3-ol | 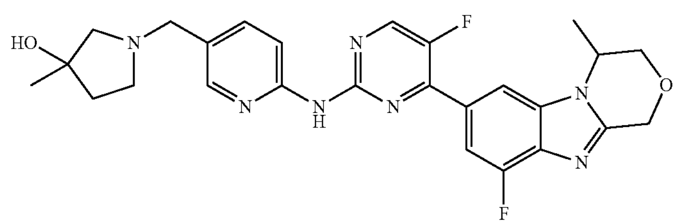 [SMILES: CC1COCc2nc3c(F)cc(-c4nc(Nc5ccc(CN6CCC(C)(O)C6)cn5)ncc4F)cc3n21] | 508.2 | 29a (+) 29b (−) |
| 30 | 5-fluoro-4-(9-fluoro-4-methyl-3,4-dihydro-1H-benzo[4,5]imidazo[2,1-c][1,4]oxazin-7-yl)-N-(5-((4-(oxetan-3-yl)piperazin-1-yl)methyl)pyridin-2-yl)pyrimidin-2-amine | 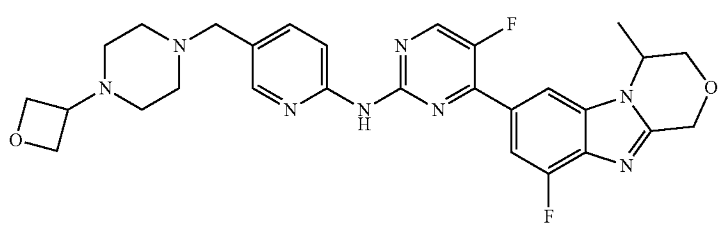 [SMILES: CC1COCc2nc3c(F)cc(-c4nc(Nc5ccc(CN6CCN(C7COC7)CC6)cn5)ncc4F)cc3n21] | 549.2 | 30a (+) 30b (−) |
| 31 | 5-fluoro-4-(9-fluoro-4-methyl-3,4-dihydro-1H-benzo[4,5]imidazo[2,1-c][1,4]oxazin-7-yl)-N-(5-(4-(oxetan-3-yl)piperazin-1-yl)pyridin-2-yl)pyrimidin-2-amine | 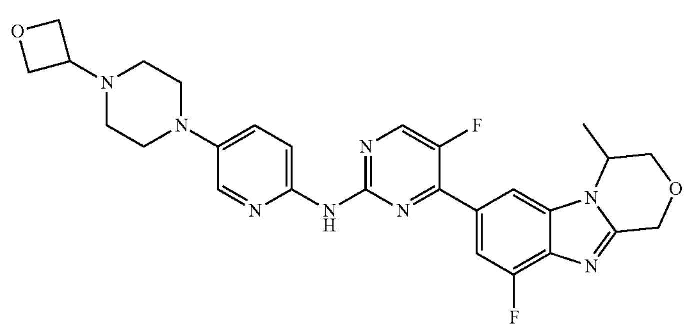 [SMILES: CC1COCc2nc3c(F)cc(-c4nc(Nc5ccc(N6CCN(C7COC7)CC6)cn5)ncc4F)cc3n21] | 535.2 | 31a (+) 31b (−) |

TABLE 9-continued

| EX No. | Chemical Name | Structure | Physical Data (MS) (M + H)+ | Enantiomers (optical rotation) |
|---|---|---|---|---|
| 32 | N-(5-((4-ethylpiperazin-1-yl)methyl)pyridin-2-yl)-5-fluoro-4-(9-fluoro-4-methyl-1,2,3,4-tetrahydrobenzo[4,5]imidazo[1,2-a]pyrazin-7-yl)pyrimidin-2-amine | 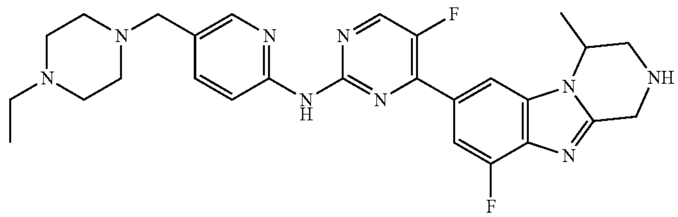 [SMILES: CCN1CCN(Cc2ccc(Nc3ncc(F)c(-c4cc(F)c5nc6n(c5c4)C(C)CNC6)n3)nc2)CC1] | 520.3 | 32a (+) 32b (−) |
| 33 | 5-fluoro-4-(9-fluoro-4-methyl-3,4-dihydro-1H-benzo[4,5]imidazo[2,1-c][1,4]oxazin-7-yl)-N-(5-((4'-methyl-[1,1'-bipiperazin]-4-yl)methyl)pyridin-2-yl)pyrimidin-2-amine | 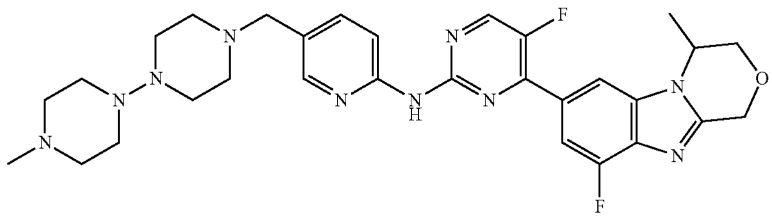 [SMILES: CC1COCc2nc3c(F)cc(-c4nc(Nc5ccc(CN6CCN(N7CCN(C)CC7)CC6)cn5)ncc4F)cc3n21] | 591.3 | 33a (+) 33b (−) |
| 34 | 5-fluoro-4-(9-fluoro-4-methyl-3,4-dihydro-1H-benzo[4,5]imidazo[2,1-c][1,4]oxazin-7-yl)-N-(5-((4-(1-methylpiperidin-4-yl)piperazin-1-yl)methyppyridin-2-yl)pyrimidin-2-amine | 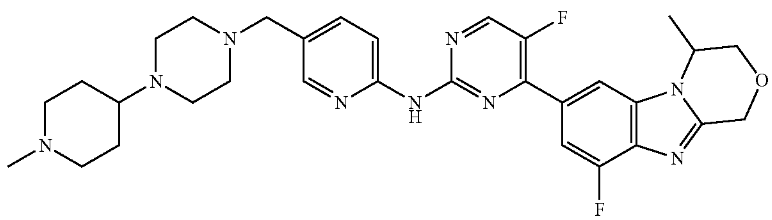 [SMILES: CC1COCc2nc3c(F)cc(-c4nc(Nc5ccc(CN6CCN(C7CCN(C)CC7)CC6)cn5)ncc4F)cc3n21] | 590.3 | 34a (+) 34b (−) |

Examples for Comparison

Prepare the following comparison examples essentially as described for Example 1, 2 or 15 using the corresponding intermediates or starting materials. For example, Prepare the following comparison example 8, 9 and 10 (shown in Table 10) essentially as described for Example 2 using

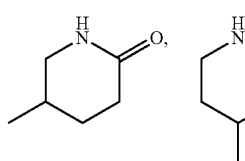

instead of

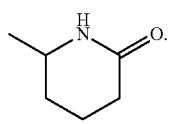

And prepare the following comparison example 7 essentially as described for Example 1 using

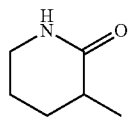

instead of

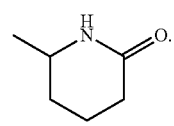

TABLE 10

| Com, EX. No. | Chemical Name | Structure | Physical Data (MS) (M + H)+ |
|---|---|---|---|
| 1 | 5-fluoro-4-(6-fluoro-3,4-dihydro-2H-spiro[benzo[4,5]imidazo,[1,2-a]pyridine-1,1'-cyclopropan]-8-yl)-N-(5-(4-methylpiperazin-1-yl)pyridin-2-yl)pyrimidin-2-amine | 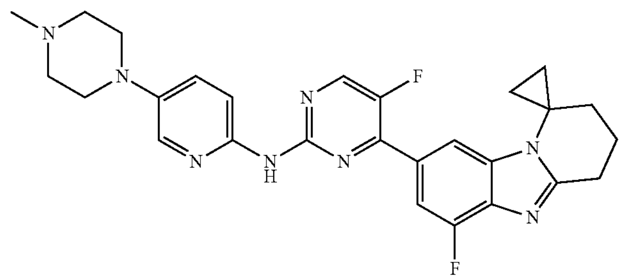 [SMILES: CN1CCN(c2ccc(Nc3ncc(F)c(-c4cc(F)c5nc6n(c5c4)C4(CCC6)CC4)n3)nc2)CC1] | 503.2 |
| 2 | 5-fluoro-4-(6-fluoro-1,2,3,4-tetrahydrobenzo[4,5]imidazo[1,2-a]pyridin-8-yl)-N-(5-(4-methylpiperazin-1-yl)pyridin-2-yl)pyrimidin-2-amine | 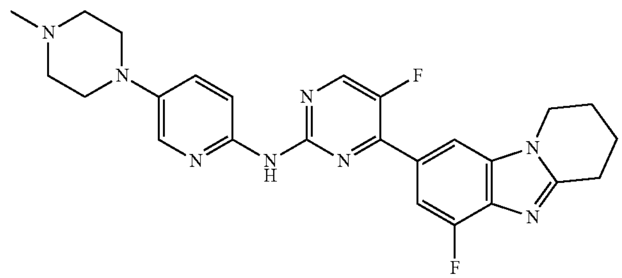 [SMILES: CN1CCN(c2ccc(Nc3ncc(F)c(-c4cc(F)c5nc6n(c5c4)CCCC6)n3)nc2)CC1] | 476.2 |
| 3b | (R)-N-(5-((4-ethylpiperazin-1-yl)methyl)pyridin-2-yl)-5-fluoro-4-(9-fluoro-4-isopropyl-3,4-dihydro-1H-benzo[4,5]imidazo[2,1-c][1,4]oxazin-7-yl)pyrimidin-2-amine | 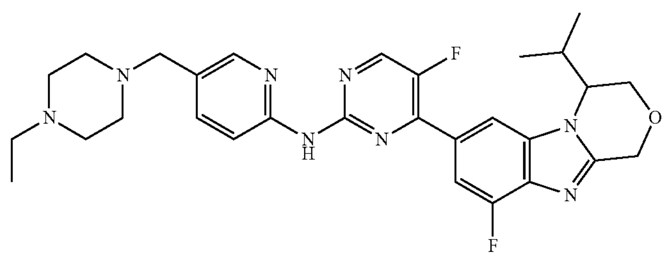 [SMILES: CCN1CCN(Cc2ccc(Nc3ncc(F)c(-c4cc(F)c5nc6n(c5c4)C(C(C)C)COC6)n3)nc2)CC1] | 548.3 |
| 4b | (R)-4-(4-ethyl-9-fluoro-3,4-dihydro-1H-benzo[4,5]imidazo[2,1-c][1,4]oxazin-7-yl)-N-(5-((4-ethylpiperazin-1-yl)methyl)pyridin-2-yl)-5-fluoropyrimidin-2-amine | 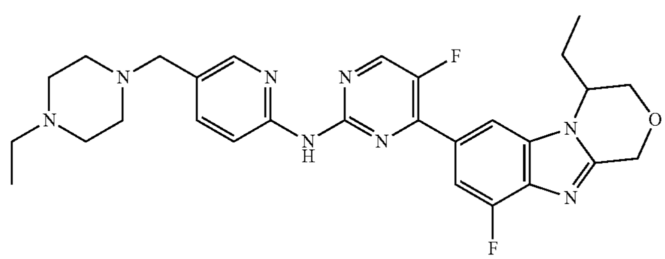 [SMILES: CCC1COCc2nc3c(F)cc(-c4nc(Nc5ccc(CN6CCN(CC)CC6)cn5)ncc4F)cc3n21] | 534.3 |
| 5 | 5-fluoro-4-(6-fluoro-1,1-dimethyl-1,2,3,4-tetrahydrobenzo[4,5]imidazo[1,2-a]pyridin-8-yl)-N-(5-(4-(oxetan-3-yl)piperazin-1-yl)pyridin-2-yl)pyrimidin-2-amine | 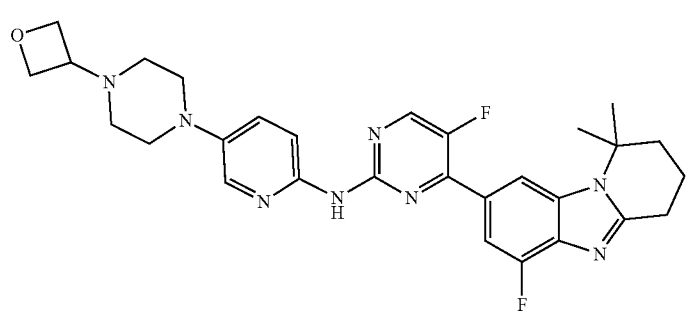 [SMILES: CC1(C)CCCc2nc3c(F)cc(-c4nc(Nc5ccc(N6CCN(C7COC7)CC6)cn5)ncc4F)cc3n21] | 546.3 |

TABLE 10-continued

| Com, EX. No. | Chemical Name | Structure | Physical Data (MS) (M + H)+ |
|---|---|---|---|
| 6 | 5-fluoro-4-(6-fluoro-1,1-dimethyl-1,2,3,4-tetrahydrobenzo[4,5]imidazo[1,2-a]pyridin-8-yl)-N-(5-(piperazin-1-ylmethyl)pyridin-2-yl)pyrimidin-2-amine | 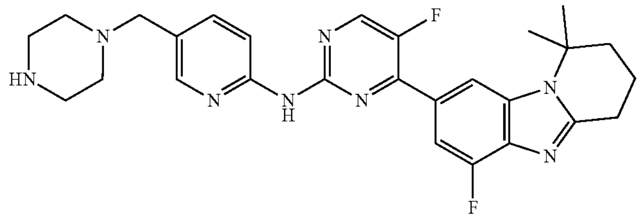 [SMILES: CC1(C)CCCc2nc3c(F)cc(-c4nc(Nc5ccc(CN6CCNCC6)cn5)ncc4F)cc3n21] | 504.3 |
| 7 | 4-(6-fluoro-4-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine | 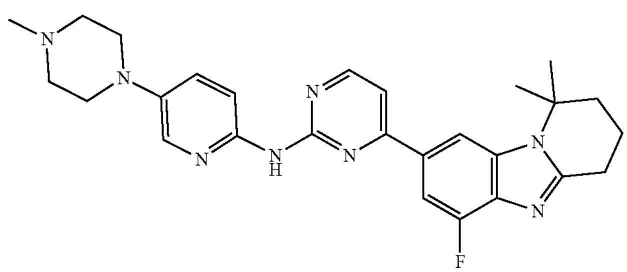 [SMILES: CN1CCN(c2ccc(Nc3nccc(-c4cc(F)c5nc6n(c5c4)C(C)(C)CCC6)n3)nc2)CC1] | 473.3 |
| 8 | N-(5-((4-ethylpiperazin-1-yl)methyl)pyridin-2-yl)-5-fluoro-4-(6-fluoro-2-methyl-1,2,3,4-tetrahydrobenzo[4,5]imidazo[1,2-a]pyridin-8-yl)pyrimidin-2-amine | 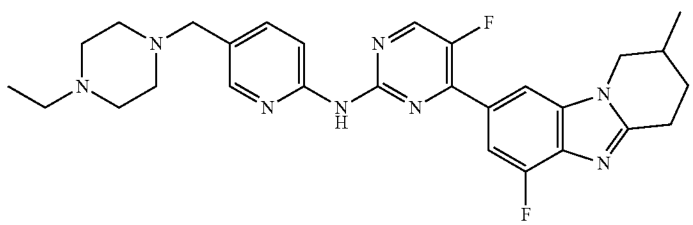 [SMILES: CCN1CCN(Cc2ccc(Nc3ncc(F)c(-c4cc(F)c5nc6n(c5c4)CC(C)CC6)n3)nc2)CC1] | 519.3 |
| 9 | N-(5((4-ethylpiperazin-1-yl)methyl)pyridin-2-yl)-5-fluoro-4-(6-fluoro-methyl-1,2,3,4-tetrahydrobenzo[4,5]imidazo[1,2-a]pyridin-8-yl)pyrimidin-2-amine | 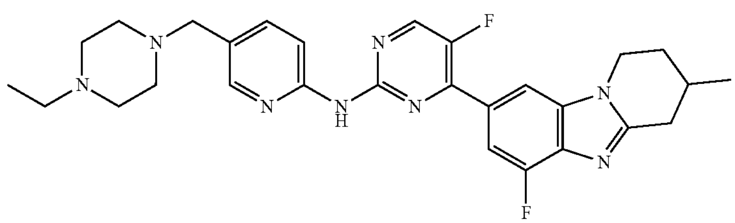 [SMILES: CCN1CCN(Cc2ccc(Nc3ncc(F)c(-c4cc(F)c5nc6n(c5c4)CCC(C)C6)n3)nc2)CC1] | 519.3 |
| 10 | N-(5((4-ethylpiperazin-1-yl)methyl)pyridin-2-yl)-5-fluoro-4-(6-fluoro-4-methyl-1,2,3,4-tetrahydrobenzo[4,5]imidazo[1,2-a]pyridin-8-yl)pyrimidin-2-amine | 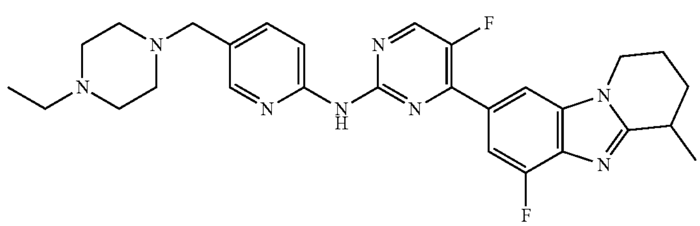 [SMILES: CCN1CCN(Cc2ccc(Nc3ncc(F)c(-c4cc(F)c5nc6n(c5c4)CCCC6C)n3)nc2)CC1] | 519.3 |

In the above table, The Con. EX. No. 3b and 4b are synthesis essentially as described for Example 15, and then test their optical rotation respectively essentially as described for Example 15-1. The Com. EX. No. 3b and 4b both show negative optical rotation.

Pharmacological Testing

The results of the following assays demonstrate evidence that the compounds exemplified herein are useful as specific CDK4/6 inhibitors and as anticancer agents. As used herein, "IC$_{50}$" refers to the concentration of an agent which produces 50% of the maximal inhibitory response possible for the agent.

For illustration conveniently, the following general structure is showed below. Surprisingly, we found that "R" has a critical influence on biological activity, selectivity and safety.

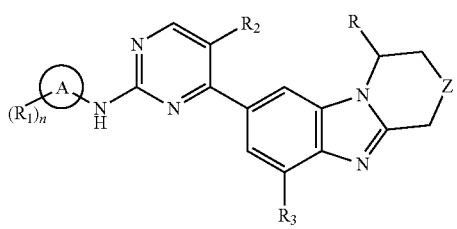

Test 1 Comparison of Different Substituent by Cell Proliferation Assay

Effects of test compounds on in vitro proliferation were measured by MTS cell viability assay.

Cell Culture

Human colorectal cancer cells (colo-205) is expanded in culture (colo-205 is grown in DMEM media with 12% FBS, 1% P/S, and 1% L-glutamine).

MTS Cell Viability Assay:

1. Seed cells at density of $4 \times 10^3$ cells per well of 96-wells plates, grow for 24 h;

2. Add varying concentrations of test compounds to the cells;

3. Incubate for 7 days of exposure;

4. Prepare reagents following the instructions in the Cell Proliferation Assay kit (Promega);

5. Change to serum-free medium with a final volume of 100 µl/well. Prepare a set of wells with medium only for background subtraction;

6. Add 20 µl MTS solution containing PMS to each well (final concentration of MTS will be 0.33 mg/mL);

7. Incubate 1 to 4 h at 37° C. in a humidified, 5% CO atmosphere;

8. Record absorbance at 490 nm using VICTOR™ X5 plate reader (PerkinElmer).

All experimental points were set up in three wells and all experiments were repeated at least three times. $IC_{50}$ value is calculated from dose-response curve by using software (Graphpad prism 6), and the results are shown in Table 11.

TABLE 11

| Sample | $IC_{50}$(colo-205)/µM |
| --- | --- |
| LY2835219 | 0.136 |
| Example 1 | 0.078 |
| Example 2 | 0.053 |
| Com. EX. 1 | 6.644 |
| Com. EX. 2 | 8.897 |

The above exemplified compounds display anti-tumor activity in this model as shown in Table 11, thus demonstrating that exemplified compounds of the present invention have more potent in vivo activity against $Rb^+$ tumors. Compared with the known compound LY2835219 (Abemaciclib), the compound of the present invention, for example the compound of Example 1 or 2 has more potent inhibition against $Rb^+$ tumors. Compared with the comparison example 1 (hereinafter referred to as Com.EX.1; R is spiro) and the comparison example 2 (hereinafter referred to as Com.EX.2; R is H), the compound of the present invention, for example the compound of Example 1 or 2 (R is methyl) has much more potent inhibition against $Rb^+$ tumors.

The above exemplified compounds also display that R is methyl but not H or spiro has much more potent biological activity in this model. From the above results, we can see that type of substituents has significant influence on inhibiting against $Rb^+$ tumors.

Test 2 Comparison of Different Substituent by Safety Test

Select compounds prepared as described above were assayed the safety according to the change on body weight and whether mortality happened, and the procedures were described herein. Testing compound is prepared in an appropriate vehicle and is administered to BALB/c mice (22-23 g) by oral gavage. Body weight and mortality are taken as general measurement of toxicity. Weight loss (% body weight changed) is calculated twice a week by comparing treated groups to vehicle control group during the course of treatment. The compound 2 and 16 demonstrates almost little weight loss, in these models when dosed at 200 mg/kg (qd). But at the same dosage, the comparison examples, for example, Com. EX. 3b and Com. EX. 4b are able to cause much more weight loss, even cause high mortality with 4 and 5 mice death in each group (6 mice) after treatment for 2 weeks.

The results were given in table 12. "*" stands for "weight loss less than 5%"; "" stands for "weight loss more than 5% and less than 10%"; "*" stands for "weight loss more than 10% and less than 30%"; "****" stands for "weight loss more than 30%". "+" stands for "mortality occurred"; "−" stands for "No mortality occurred".

TABLE 12

| Sample | Body weight | observation |
| --- | --- | --- |
| LY2835219 | * | − |
| Example 2b | * | − |
| Example 16b | * | − |
| Com. EX. 3b | *** | + |
| Com. EX. 4b | *** | + |

Surprisingly, we found that Con. EX.3b (R is isopropyl) or Con. EX.4b (R is ethyl) has more side effects and toxicity. However, the exemplified compounds of the present invention, for example compound 2b or 16b (R is methyl), are much safer, thus demonstrating that type of substituents has significant influence on safety.

Test 3 the Effect of Number of Substituent by CDK Kinase Assays

To demonstrate that the compounds exhibit affinity for CDK kinases (CDK2/CycA2, CDK4/CycD3, CDK6/cycD3), CDK kinase assays were performed.

Reaction buffers were prepared as follows: kinase base buffer for CDK2,6 (50 mM HEPES, pH 7.5; 0.0015% Brij-35; 10 mM $MgCl_2$; 2 mM DTT); Kinase base buffer for CDK4 (20 mM HEPES, pH 7.5; 0.01% Triton X-100; 10 mM $MgCl_2$; 2 mM DTT); Stop buffer (100 mM HEPES, pH 7.5; 0.015% Brij-35; 0.2% Coating Reagent #3; 50 mM EDTA).

Enzyme Reaction Protocol:

1) Dilute the compound to 50X of the final desired highest concentration in reaction by 100% DMSO. Transfer 100 µL of this compound dilution to a well in a 96-well plate. Then, serially dilute the compound by transferring 30 µL to 60 µL of 100% DMSO in the next well and so forth for a total of 10 concentrations. Add 100 µL of 100% DMSO to two empty wells for no compound control and no enzyme control in the same 96-well plate. Mark the plate as source plate.

2) Prepare intermediate plate by transferring 10 µL of compound from source plate to a new 96-well plate containing 90 µL of kinase buffer as the intermediate plate.

3) Transfer 5 μL of compound from the 96-well intermediate plate to a 384-well plate in duplicates.

4) Add 10 μL of 2.5× enzyme solution to each well of the 384-well assay plate.

5) Incubate at room temperature for 10 min.

6) Add 10 μL of 2.5× substrate solution prepared by adding FAM-labeled peptide and ATP in the kinase base buffer. Reaction concentrations for enzymes and substrates as following table (Table 13):

TABLE 13

| Enzyme | Enzyme (nM) | ATP (μM) | Peptide | Peptide concentration(μM) |
|---|---|---|---|---|
| CDK2 | 10 | 30 | P18 | 3 |
| CDK4 | 10 | 280 | P8 | 3 |
| CDK6 | 15 | 800 | P8 | 3 |

7) Incubate at 28° C. for specified period of time.

8) Add 25 μL of stop buffer to stop reaction.

9) Collect data on Caliper. Then convert conversion values to inhibition values.

Percent inhibition=(max−conversion)/(max−min)*100.

"max" stands for DMSO control and "min" stands for low control herein.

10) Curve fitting using percent inhibition in XLFit excel add-in version 4.3.1 to obtain $IC_{50}$ values. Equation used is: Y=Bottom+(Top−Bottom)/(1+($IC_{50}$/X)^HillSlope).

Wherein, Y is inhibition percentage (%); X is concentration of the test compound.

The results are expressed as $IC_{50}$ value which is shown in Table 14.

TABLE 14

| Sample | $IC_{50}$(CDK2)/μM | $IC_{50}$(CDK4)/μM | $IC_{50}$(CDK6)/μM |
|---|---|---|---|
| LY2835219 | 0.039 | 0.002 | 0.022 |
| Example 1 | >0.3 | 0.002 | 0.023 |
| Example 2 | >0.3 | 0.002 | 0.031 |
| Example 16b | >0.3 | 0.003 | 0.040 |
| Com. EX. 5 | 0.040 | 0.003 | 0.017 |
| Com. EX. 6 | 0.040 | 0.007 | 0.014 |

As shown in the above table, we can see the number of methyl has very important influence on selectivity. Surprisingly, the exemplified compounds of the present invention display an $IC_{50}$ of >0.3 μM in the above CDK2 kinase inhibition assay and an $IC_{50}$ of ≤0.04 μM in the above CDK4/6 kinase inhibition assay as shown in Table 14. It demonstrates that the exemplified compounds of the present invention are more selective inhibitors of CDK4/6 kinase activity. Thus it shows that the exemplified compounds (R represents only one methyl) are more specific inhibitors of CDK4/6, compared with the known compound LY2835219 and comparison example, for example Com. EX. 5 or Com. EX. 6 (R represents two methyl).

Test 4 the Effect of Substituent Site

Select compound prepared as described above were assayed according to the biological procedures described herein. The results were showed as in below table.

TABLE 15

| Sample | Structure | $IC_{50}$(CDK4)/μM | $IC_{50}$(CDK6)/μM |
|---|---|---|---|
| Example 1 | 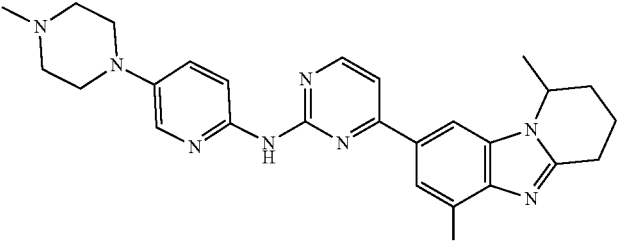 | 0.002 | 0.023 |
| Com. EX. No. 7 | 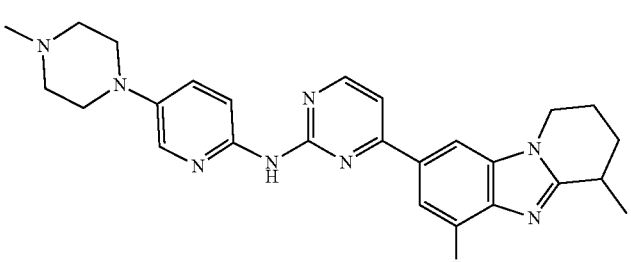 | 0.057 | 0.110 |

Further, a Head-to-Head comparison of Example 2 and its comparison example 8, 9 or 10 was shown in the following table. The results were given in table 16. "++++" stands for "IC$_{50}$ value less than 0.2 μM"; "+++" stands for "IC$_{50}$ value more than 0.2 μM and less than 1.0 μM"; "++" stands for "IC$_{50}$ value more than 1.0 μM and less than 2.0 μM"; "+" stands for "IC$_{50}$ value more than 2.0 μM".

TABLE 16

| Sample | Structure | IC$_{50}$(CDK4)/μM |
|---|---|---|
| Example 2 | (structure) | ++++ |
| Com. EX. No. 8 | (structure) | ++ |
| Com. EX. No. 9 | (structure) | ++ |
| Com. EX. No. 10 | (structure) | ++ |

TABLE 17

| Example | IC$_{50}$(CDK4)/nM | IC$_{50}$(CDK6)/nM |
|---|---|---|
| LY2835219 | 2 | 22 |
| Compound 1a | 3.0 | 121 |
| Compound 2a | 4.1 | 108 |
| Compound 15a | 6.7 | 230 |
| Compound 16a | 17.6 | >300 |
| Compound 1b | 1.7 | 23 |
| Compound 2b | 1.9 | 22 |
| Compound 15b | 1.8 | 23 |
| Compound 16b | 3.4 | 45 |

As shown in the above table 15 and 16, we can see substituent site also plays an important role on biological activity. The effect on biological activity resulting from the site change of substituents is significantly unexpected.

As shown in the results presented above, we can know that "R" of the 6-membered heterocyclic ring has a critical influence on biological activity, selectivity and safety. Surprisingly, when there is one and only one methyl in the said 6-membered heterocyclic ring, the effects will be obtained at least as follows:

① improved biological activity;
② good selective; and
③ low side effects.

Test 5 the Effect of Opticity

Select compounds prepared as described above were assayed according to the biological procedures described as Test 3 (CDK kinase assays). The results were showed as in below table.

As shown in the above table, we can see compound 1b, 2b, 16b is more potent than compound 1a, 2a, 15a, 16a in inhibiting CDK4/6 respectively, thus demonstrating that (−) enantiomers of the present compounds are advantageous over the (+) enantiomers.

In some instances, the compound disclosed herein is administered where one enantiomer [e.g., the (−) enantiomer or (+) enantiomer] is present in high enantiomeric excess. In one instance, the enantiomer of compound 1b having a negative optical rotation, e.g., −35.394° (c=3.0 mg/mL, EtOH) has greater activity against CDK4/6 enzyme than the enantiomer (compound 1a) that has a positive optical rotation of +30.325° (c=3.0 mg/mL, EtOH). In another instance, the enantiomer of compound 2b having a negative optical rotation, e.g., −32.036° (c=4.0 mg/mL, DCM) has greater activity against CDK4/6 enzyme than the enantiomer that has a positive optical rotation of +38.088° (c=4.0 mg/n, DCM). In other instances, the enantiomer of compound 15b having a negative optical rotation, e.g., −28.929° (c=4.6 mg/mL, DCM/MeOH=1:1) has greater activity against CDK4/6 enzyme than the enantiomer that has a positive optical rotation of +32.829° (c=4.6 mg/mL, DCM/MeOH=1:1).

Test 6 Inhibitory Activity and Selectivity Test on Other Subtypes of CDK Kinase at Molecular Level The representative compound 2b of the present invention was used as a test compound, and compared with the positive control drug LY2835219 (Abemaciclib) to compare CDK kinase inhibitory activity and selective specificity between them.

The mechanism of this method is shown in formula (II). The kinase catalyzes the phosphorylation of the protein substrate to label the $^{33}$P on the $^{33}$P-labeled ATP (γ-$^{33}$P-ATP) to the protein substrate in the reaction system; the reaction system was spotted on P81 ion-exchange membrane, and the membrane was washed extensively with 0.75% phosphate buffer; the radioactively-phosphorylated substrate was left on the membrane, and the kinase activity was reflected by recording the intensity of the substrate protein radiolabel.

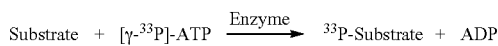

Formula (II)

Data was processed with Prism4 Software (GraphPad), and the curve fitting formula was:

Y=Bottom+(Top−Bottom)/(1+10^((Log IC$_{50}$−X)*Hill-Slope)); wherein, Y is percent inhibition (%); X is logarithm of concentration of the inhibitor.

Results: Through the screening of various CDK kinases, it was found that the representative compound 2, 2a, and 2b have an IC$_{50}$ of greater than 0.4 μM for inhibiting CDK1/2/7/9, which is tens to thousands of fold higher than that of CDK4/6. (See table 18)

TABLE 18

CDK kinase inhibitory activity

| | IC$_{50}$(nM) | | | |
|---|---|---|---|---|
| Kinase | LY2835219 | Compound 2 | Compound 2a | Compound 2b |
| CDK1/cyclin B | 308 | 2350 | 3573 | 1683 |
| CDK2/cyclin E | 90 | 474 | 596 | 441 |
| CDK7/cyclin H | 2071 | 1050 | 2370 | 664 |
| CDK9/cyclin T1 | 111 | 572 | 779 | 649 |

Conclusion: At the molecular level, the representative compound 2 and compound 2b of the present invention showed strong inhibitory effect on CDK4/6 and weak inhibitory effect on CDK1/2/7/9, indicating that compound 2 and compound 2b is a CDK4/6 kinase inhibitor with excellent selectivity. Compound 2a showed strong inhibitory effect on CDK4, slight inhibitory effect on CDK6, and very weak inhibitory effect on CDK1/2/7/9, indicating that compound 2a is a CDK4 kinase inhibitor with extreme selectivity and a CDK6 kinase inhibitor with good selectivity. Additionally, the selectivity of the representative compounds of the present invention between CDK1/2/9 and CDK4/6 was significantly higher than that of LY2835219 (Abemaciclib).

Test 7 Tumor Regression Effect on JeKo-1 Xenograft Animal Model

JeKo-1 cells were cultured in RPMI 1640 medium containing 20% fetal bovine serum. Exponentially growing JeKo-1 cells were collected and resuspended in PBS to a suitable concentration for NOD/SCID mice subcutaneous tumor inoculation. Seventy female mice were inoculated subcutaneously on the right with 5×10$^6$ JeKo-1 cells, resuspended in PBS and matrigel (1:1). When the average tumor volume reached 134 mm$^3$, the mice were randomly grouped according to the size of the tumor and were administrated. Forty-eight mice were divided into the experimental group, and the remaining twenty-two mice were not used for experiment. Tumor volume is calculated as: long diameter× short diameter$^2$/2. The test was divided into solvent control group, test drug representative compound 2b (10 mg/kg), test drug representative compound 2b (25 mg/kg), test drug representative compound 2b (50 mg/kg), test drug representative compound 2b (100 mg/kg), a total of 6 groups with each of 8 mice, and the mice were administered orally by gavage once a day and then continuous administration for 19 days. Efficacy is evaluated according to the relative tumor growth inhibition rate of TGI.

The calculation formula is as follows: TGI (%)=(C−T)/C×100% (C and T are the average tumor weight of the solvent control group and the average tumor weight of the treatment group, respectively). The higher the TGI (%) value illustrates the better the potency; and vice versa.

Results: Compound 2b demonstrates excellent anti-tumor activity.

TABLE 19

Anti-tumor efficacy evaluation of representative compound 2b on JeKo-1 xenograft model

| Group | Dose (mg/kg) | Relative tumor growth inhibition rate(TGI(%)) | p Value$^a$ |
|---|---|---|---|
| Solvent control | — | — | — |
| Compound 2b | 10 | 42.7 | 0.087 |
| Compound 2b | 25 | 73.8 | 0.003 |
| Compound 2b | 50 | 98.3 | 0.001 |
| Compound 2b | 100 | 104.5 | 0.001 |

Note:
a: p value is the comparative analysis of tumor volume for the treatment group and the solvent control group.

Accordingly, in some instances, it is beneficial to administer to a subject a compound 1, 2 or 15 having a high enantiomeric excess of the enantiomer having a negative optical rotation to treat a disease. Unexpectedly, the optically pure (−) enantiomer of the present compound, including but not limited to compound 1b, 2b or 15b is more potent drug for treating a disease mediated by CDK4/6 in a subject.

A number of embodiments of the invention have been described. Nevertheless, it will be understood that various modifications may be made without departing from the spirit and scope of the invention. Other embodiments are in the claims.

What is claimed is:

1. A compound of Formula I, or a stereoisomer, a tautomer, a polymorph, a solvate, a pharmaceutically acceptable salt, or a prodrug thereof,

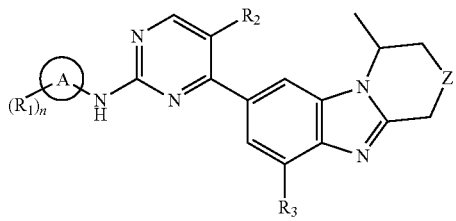

Formula I wherein,
ring A is aryl or heteroaryl;
Z is selected from the group consisting of $CH_2$, NH, O and S;
$R_1$ is independently selected from the group consisting of hydrogen, halogen, CN, $NO_2$, OH, $NH_2$, $C_{1-8}$alkyl, $C_{1-8}$alkoxy, $C_{3-8}$cycloalkyl, aryl, heteroaryl, heterocyclyl, heterocyclyl-$(CH_2)_m$—, aryl-$C_{1-6}$alkyl-, heteroaryl-$C_{1-6}$alkyl-, —$NR_{12}R_{13}$, —$NR_{12}$-$C_{1-6}$alkylene-$NR_{12}R_{13}$, and heterocyclyl-C(O)—, wherein the $C_{1-8}$alkyl, $C_{1-8}$alkoxy, $C_{3-8}$cycloalkyl, aryl, heteroaryl, heterocyclyl, heterocyclyl-$(CH_2)_m$—, aryl-$C_{1-6}$alkyl-, heteroaryl-$C_{1-6}$alkyl-, or heterocyclyl-C(O)— are each unsubstituted or substituted with at least one substituent selected from halogen, hydroxyl, $C_{1-8}$alkyl, $C_{3-8}$cycloalkyl, heterocyclyl, —$NR_{12}R_{13}$, or —$(CH_2)_t$—OH;
$R_2$ and $R_3$ are each independently selected from H, OH, CN, $NO_2$, $NH_2$, halogen, $C_{1-8}$alkyl, $C_{1-8}$alkoxy, $C_{3-8}$cycloalkyl, aryl, heteroaryl, heterocyclyl; wherein the $C_{1-8}$alkyl, $C_{1-8}$alkoxy, $C_{3-8}$cycloalkyl, aryl, heteroaryl, heterocyclyl are each unsubstituted or substituted with at least one substituent selected from halogen, hydroxyl, $C_{1-8}$alkyl, $C_{3-8}$cycloalkyl, or heterocyclyl;
$R_{12}$ and $R_{13}$ are each independently selected from H, $C_{1-8}$alkyl, aryl, heteroaryl, heterocyclyl, $C_{3-8}$cycloalkyl; wherein the $C_{1-8}$alkyl, aryl, heteroaryl, heterocyclyl, or $C_{3-8}$cycloalkyl are each unsubstituted or substituted with at least one substituent selected from halogen, hydroxyl, $C_{1-8}$alkyl, $C_{3-8}$cycloalkyl, or heterocyclyl;
m is 0, 1, 2, 3 or 4;
n is 0, 1, 2, 3 or 4;
t is 0, 1, 2, 3 or 4.

2. The compound of claim 1, wherein Z is $CH_2$.
3. The compound of claim 1, wherein Z is O.
4. The compound of claim 1, wherein the ring A is a 6-membered heteroaryl comprising one or two heteroatoms of N.
5. The compound of claim 1, wherein the ring A is pyridyl, pyrimidinyl, or pyridazinyl.
6. The compound of claim 1, wherein the ring A is

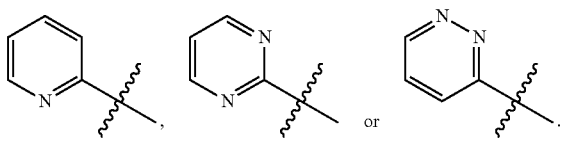 [SMILES: *c1ccccn1 ; *c1ncccn1 ; *c1cccnn1]

7. The compound of claim 1, wherein $R_1$ is heterocyclyl-$(CH_2)_m$—, or heterocyclyl-$(CH_2)_m$— substituted with $C_{1-8}$alkyl, $NR_{12}R_{13}$, 4 to 6-membered heterocyclyl, $C_{3-6}$cycloalkyl, or $(CH_2)_t$—OH.

8. The compound of claim 1, wherein $R_1$ is 5 to 6-membered heterocyclyl-$CH_2$—, or 5 to 6-membered heterocyclyl-$CH_2$— substituted with $C_{1-3}$alkyl, —$N(CH_3)_2$, —$N(CH_2CH_2OH)CH_3$,

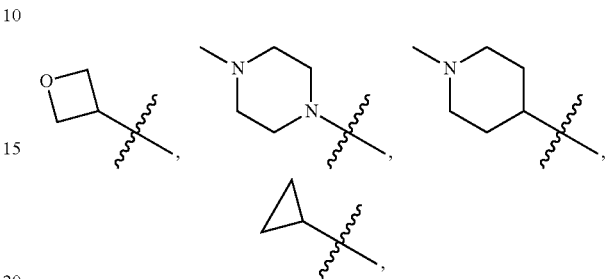

—$CH_2OH$, —$CH_2CH_2OH$, or OH.

9. The compound of claim 1, wherein $R_1$ is 6-membered heterocyclyl-$CH_2$—, or 6-membered heterocyclyl-$CH_2$— substituted with methyl or ethyl.

10. The compound of claim 1, wherein $R_1$ is heterocyclyl, or heterocyclyl substituted with $C_{1-8}$alkyl, $NR_{12}R_{13}$, 4 to 6-heterocyclyl, $C_{3-6}$cycloalkyl, or $(CH_2)_t$—OH.

11. The compound of claim 1, wherein $R_1$ is 5 to 6-membered heterocyclyl, or 5 to 6-membered heterocyclyl substituted with $C_{1-3}$alkyl, —$N(CH_3)_2$, —$N(CH_2CH_2OH)CH_3$,

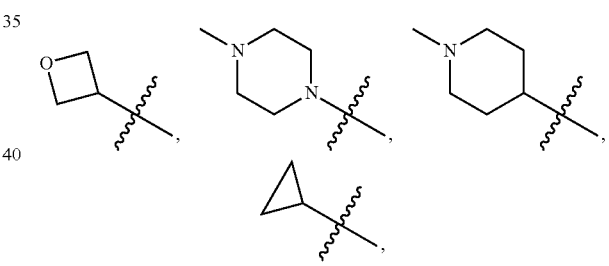

—$CH_2OH$, —$CH_2CH_2OH$, or OH.

12. The compound of claim 1, wherein $R_1$ is 6-membered heterocyclyl, or 6-membered heterocyclyl substituted with methyl or ethyl.

13. The compound of claim 1, wherein $R_1$ is 6-membered heterocyclyl-C(O)— or 6-membered heterocyclyl-C(O)— substituted with $C_{1-3}$alkyl.

14. The compound of claim 1, wherein $R_1$ is 6-membered heterocyclyl-C(O)— substituted with methyl.

15. The compound of claim 1, wherein the heterocyclyl comprises one or two heteroatoms of N or O as ring atoms.

16. The compound of claim 1, wherein the heterocyclyl comprises one or two heteroatoms of N as ring atoms.

17. The compound of claim 1, wherein $R_1$ is —$NR_{12}$—$C_{1-3}$alkylene-$NR_{12}R_{13}$.

18. The compound of claim 1, wherein $R_{12}$ and $R_{13}$ are each independently H, $(CH_2)_t$—OH or $C_{1-3}$alkyl.

19. The compound of claim 1, wherein $R_{12}$ and $R_{13}$ are each independently OH, $CH_2CH_2OH$, methyl or ethyl.

20. The compound of claim 1, wherein $R_1$ is

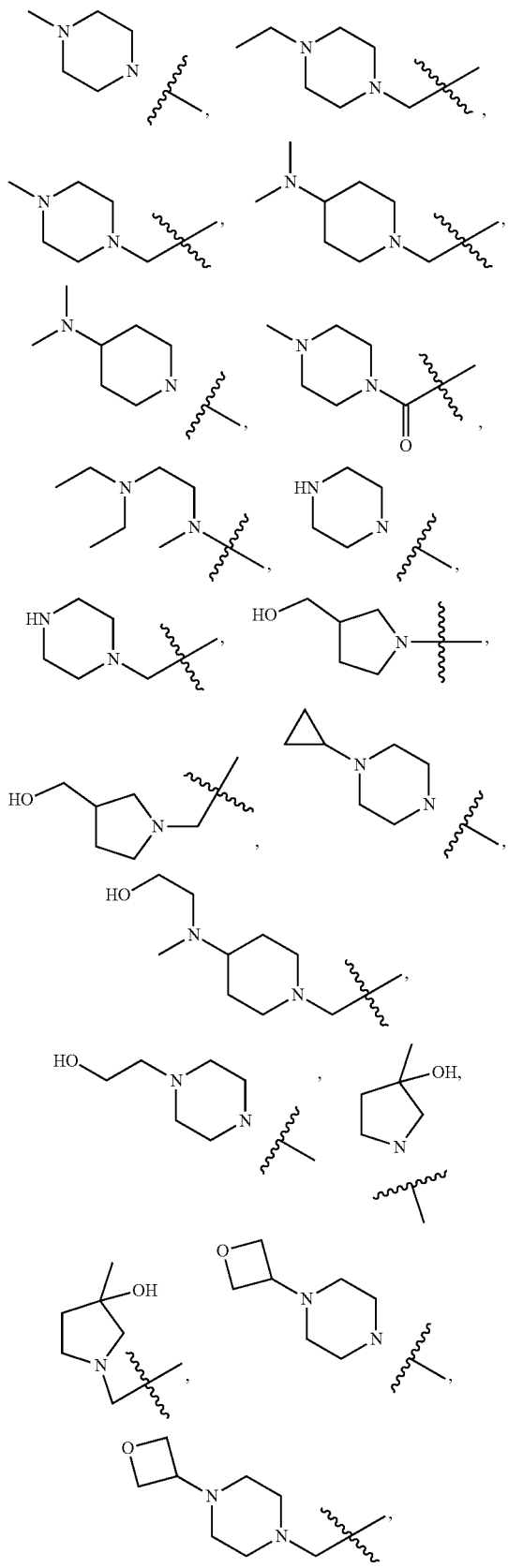

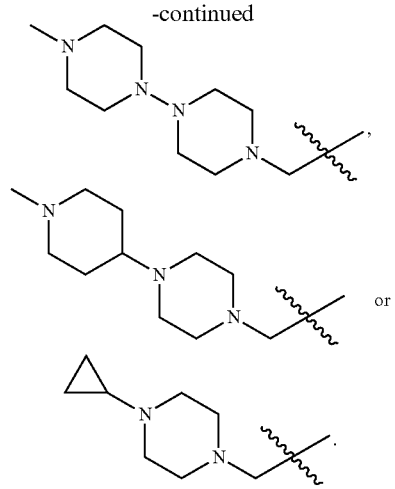

21. The compound of claim 1, wherein m is 1.
22. The compound of claim 1, wherein n is 1.
23. The compound of claim 1, wherein t is 0, 1, or 2.
24. The compound of claim 1, wherein $R_2$ and $R_3$ are each independently H, OH, halogen, $C_{1-6}$alkyl, $C_{1-6}$alkyl substituted with halogen, $C_{1-6}$alkoxy, $C_{1-6}$alkoxy substituted with halogen.
25. The compound of claim 1, wherein $R_2$ and $R_3$ are each independently H, OH, F, Cl, $CH_3$, $CH_2CH_3$, $CF_3$, $OCH_3$, or $OCF_3$.
26. The compound of claim 1, wherein $R_2$ and $R_3$ are both F.
27. The compound of claim 1, wherein the compound is:
1) 4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl) pyrimidin-2-amine;
2) N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine;
3) 5-fluoro-4-(6-fluoro-1-methyl-1,2,3,4-tetrahydrobenzo[4,5]imidazo[1,2-a]pyridin-8-yl)-N-(5-(4-methylpiperazin-1-yl)pyridin-2-yl)pyrimidin-2-amine;
4) 5-fluoro-4-(6-fluoro-1-methyl-1,2,3,4-tetrahydrobenzo[4,5]imidazo[1,2-a]pyridin-8-yl)-N-(6-((4-methylpiperazin-1-yl)methyl)pyridin-3-yl)pyrimidin-2-amine;
5) 5-fluoro-4-(6-fluoro-1-methyl-1,2,3,4-tetrahydrobenzo[4,5]imidazo[1,2-a]pyridin-8-yl)-N-(5-((4-methylpiperazin-1-yl)methyl)pyrimidin-2-yl)pyrimidin-2-amine;
6) N-(5-((4-(dimethylamino)piperidin-1-yl)methyl)pyrimidin-2-yl)-5-fluoro-4-(6-fluoro-1-methyl-1,2,3,4-tetrahydrobenzo[4,5]imidazo[1,2-a]pyridin-8-yl)pyrimidin-2-amine;
7) N-(5-((4-(dimethylamino)piperidin-1-yl)methyl) pyridin-2-yl)-5-fluoro-4-(6-fluoro-1-methyl-1,2,3,4-tetrahydrobenzo[4,5]imidazo[1,2-a]pyridin-8-yl)pyrimidin-2-amine;
8) N-(5-(4-(dimethylamino)piperidin-1-yl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine;
9) (2-((5-fluoro-4-(6-fluoro-1-methyl-1,2,3,4-tetrahydrobenzo[4,5]imidazo[1,2-a]pyridin-8-yl)pyrimidin-2-yl)amino)pyrimidin-5-yl)(4-methylpiperazin-1-yl) methanone;
10) (6-((5-fluoro-4-(6-fluoro-1-methyl-1,2,3,4-tetrahydrobenzo[4,5]imidazo[1,2-a]pyridin-8-yl)pyrimidin-2-yl)amino)pyridin-3-yl)(4-methylpiperazin-1-yl)methanone;

11) N₅-(2-(diethylamino)ethyl)-N₂-(5-fluoro-4-(6-fluoro-1-methyl-1,2,3,4-tetrahydrobenzo[4,5]imidazo[1,2-a]pyridin-8-yl)pyrimidin-2-yl)-N₅-methylpyridine-2,5-diamine;

12) N-(5-((4-ethylpiperazin-1-yl)methyl)pyridin-2-yl)-4-(6-fluoro-1-methyl-1,2,3,4,4a,5-hexahydrobenzo[4,5]imidazo[1,2-a]pyridin-8-yl)-5-(trifluoromethyl)pyrimidin-2-amine;

13) N-(5-((4-ethylpiperazin-1-yl)methyl)pyridin-2-yl)-4-(6-fluoro-1-methyl-1,2,3,4,4a,5-hexahydrobenzo[4,5]imidazo[1,2-a]pyridin-8-yl)-5-methylpyrimidin-2-amine;

14) 5-chloro-N-(5-((4-ethylpiperazin-1-yl)methyl)pyridin-2-yl)-4-(6-fluoro-1-methyl-1,2,3,4-tetrahydrobenzo[4,5]imidazo[1,2-a]pyridin-8-yl)pyrimidin-2-amine;

15) 5-fluoro-4-(9-fluoro-4-methyl-3,4-dihydro-1H-benzo[4,5]imidazo[2,1-c][1,4]oxazin-7-yl)-N-(5-(4-methylpiperazin-1-yl)pyridin-2-yl)pyrimidin-2-amine;

16) N-(5-((4-ethylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

17) N-(5-(4-(dimethylamino)piperidin-1-yl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

18) N-(5-((4-(dimethylamino)piperidin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

19) 5-fluoro-4-(9-fluoro-4-methyl-3,4-dihydro-1H-benzo[4,5]imidazo[2,1-c][1,4]oxazin-7-yl)-N-(5-(piperazin-1-yl)pyridin-2-yl)pyrimidin-2-amine;

20) 5-fluoro-4-(9-fluoro-4-methyl-3,4-dihydro-1H-benzo[4,5]imidazo[2,1-c][1,4]oxazin-7-yl)-N-(5-(piperazin-1-ylmethyl)pyridin-2-yl)pyrimidin-2-amine;

21) N-(5-fluoro-4-(9-fluoro-4-methyl-3,4-dihydro-1H-benzo[4,5]imidazo[2,1-c][1,4]oxazin-7-yl)pyrimidin-2-yl)-6-(4-methylpiperazin-1-yl)pyridazin-3-amine;

22) 6-((4-ethylpiperazin-1-yl)methyl)-N-(5-fluoro-4-(9-fluoro-4-methyl-3,4-dihydro-1H-benzo[4,5]imidazo[2,1-c][1,4]oxazin-7-yl)pyrimidin-2-yl)pyridazin-3-amine;

23) (1-(6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)pyrrolidin-3-yl)methanol;

24) (1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)pyrrolidin-3-yl)methanol;

25) N-(5-(4-cyclopropylpiperazin-1-yl) pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

26) N-(5-((4-cyclopropylpiperazin-1-yl)methyl)pyridin-2-yl)-5-fluoro-4-(9-fluoro-4-methyl-3,4-dihydro-1H-benzo[4,5]imidazo[2,1-c][1,4]oxazin-7-yl)pyrimidin-2-amine;

27) 2-((1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)piperidin-4-yl)(methyl)amino)ethan-1-ol;

28) 1-(6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)-3-methylpyrrolidin-3-ol;

29) 1-((6-((5-fluoro-4-(9-fluoro-4-methyl-3,4-dihydro-1H-benzo[4,5]imidazo[2,1-c][1,4]oxazin-7-yl)pyrimidin-2-yl)amino)pyridin-3-yl)methyl)-3-methylpyrrolidin-3-ol;

30) 5-fluoro-4-(9-fluoro-4-methyl-3,4-dihydro-1H-benzo[4,5]imidazo[2,1-c][1,4]oxazin-7-yl)-N-(5-((4-(oxetan-3-yl)piperazin-1-yl)methyl)pyridin-2-yl)pyrimidin-2-amine;

31) 5-fluoro-4-(9-fluoro-4-methyl-3,4-dihydro-1H-benzo[4,5]imidazo[2,1-c][1,4]oxazin-7-yl)-N-(5-(4-(oxetan-3-yl)piperazin-1-yl)pyridin-2-yl)pyrimidin-2-amine;

32) N-(5-((4-ethylpiperazin-1-yl)methyl)pyridin-2-yl)-5-fluoro-4-(9-fluoro-4-methyl-1,2,3,4-tetrahydrobenzo[4,5]imidazo[1,2-a]pyrazin-7-yl)pyrimidin-2-amine;

33) 5-fluoro-4-(9-fluoro-4-methyl-3,4-dihydro-1H-benzo[4,5]imidazo[2,1-c][1,4]oxazin-7-yl)-N-(5-((4'-methyl-[1,1'-bipiperazin]-4-yl)methyl)pyridin-2-yl)pyrimidin-2-amine;

34) 5-fluoro-4-(9-fluoro-4-methyl-3,4-dihydro-1H-benzo[4,5]imidazo[2,1-c][1,4]oxazin-7-yl)-N-(5-((4-(1-methylpiperidin-4-yl) piperazin-1-yl)methyl) pyridin-2-yl)pyrimidin-2-amine.

28. The compound of claim 1, wherein the compound is the (−) enantiomer of the compound.

29. The compound of claim 1, wherein the compound is the (+) enantiomer of the compound.

30. A pharmaceutical composition comprising a therapeutically effective amount of the compound according to claim 1, and a pharmaceutically acceptable excipient.

31. The pharmaceutical composition according to claim 30, wherein a weight ratio of the said compound to the said excipient is in the range from about 0.001 to about 10.

32. A method of treating a disease mediated by CDK in a subject, comprising administering the compound of claim 1 or the pharmaceutical composition comprising a therapeutically effective amount of the compound according to claim 1 and a pharmaceutically acceptable excipient, wherein the disease mediated by CDK is cancer, wherein the cancer is colon cancer, rectal cancer, mantle cell lymphoma, multiple myeloma, breast cancer, prostate cancer, glioblastoma, squamous cell esophageal cancer, liposarcoma, T-cell lymphoma melanoma, pancreatic cancer, brain cancer or lung cancer.

33. The method of claim 32, wherein the subject is a human.

* * * * *

UNITED STATES PATENT AND TRADEMARK OFFICE
CERTIFICATE OF CORRECTION

| | |
|---|---|
| PATENT NO. | : 11,053,238 B2 |
| APPLICATION NO. | : 16/471415 |
| DATED | : July 6, 2021 |
| INVENTOR(S) | : Wang et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

In the Specification

In Column 4, Line number 60, please replace " 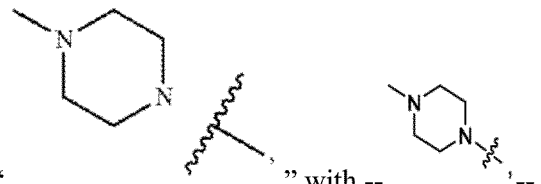 " with -- 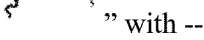 --.

In Column 5, Line number 5, please replace " 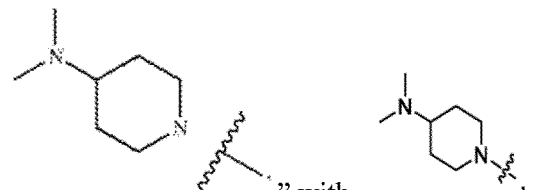 " with -- 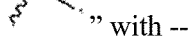 --.

In Column 5, Line number 10, please replace " 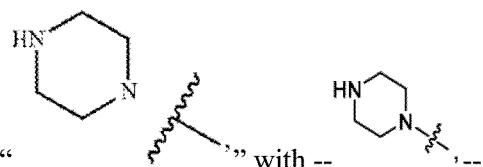 " with -- 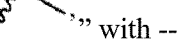 --.

Signed and Sealed this
First Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)

In Column 5, Line number 20, please replace " 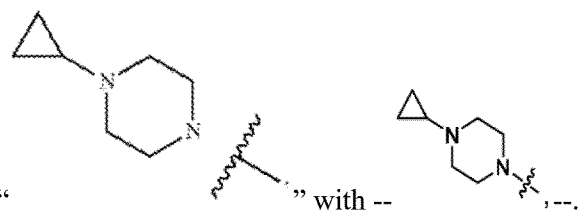 " with -- , --.

In Column 5, Line number 35, please replace " 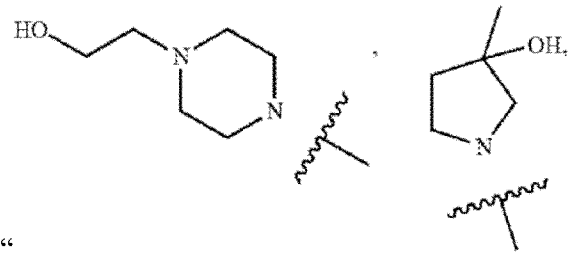 " with -- 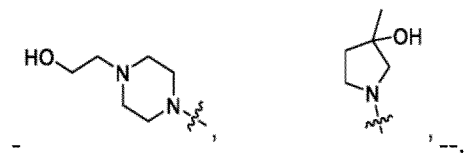 , --.

In Column 5, Line number 45, please replace " 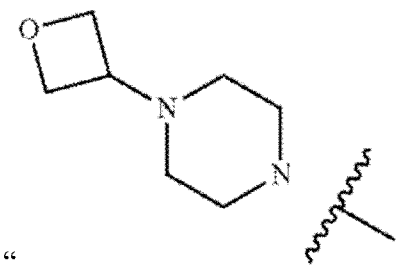 " with -- 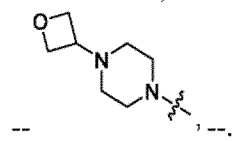 , --.

In the Claims

In Claim 20, Column 67, Line number 5, please replace " 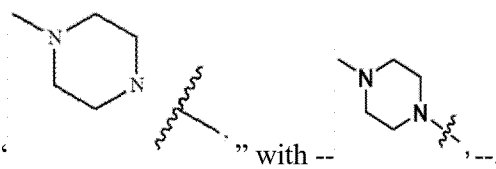 " with -- , --.

In Claim 20, Column 67, Line number 20, please replace " 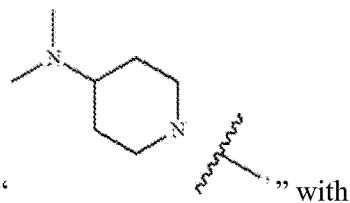 " with

CERTIFICATE OF CORRECTION (continued)
U.S. Pat. No. 11,053,238 B2

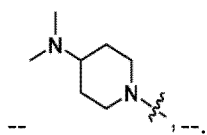

In Claim 20, Column 67, Line number 25, please replace " 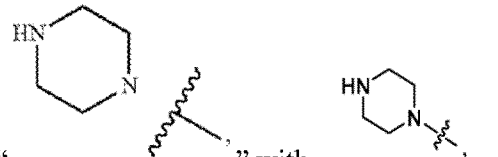 " with -- , --.

In Claim 20, Column 67, Line number 35, please replace " 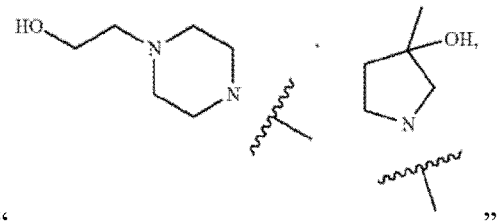 " with

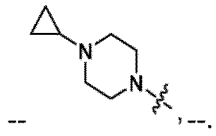

-- , --.

In Claim 20, Column 67, Line number 50, please replace " 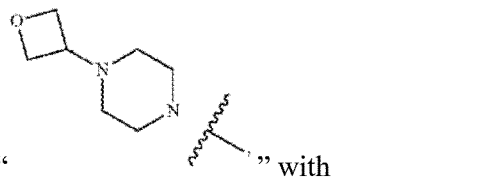 "

with -- 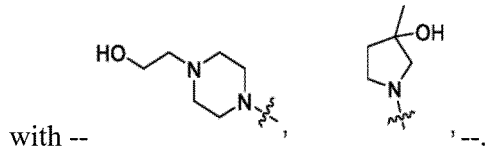 , --.

In Claim 20, Column 67, Line number 55, please replace " " with

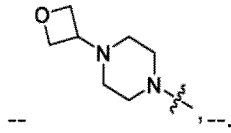

-- , --.